(12) United States Patent
Chase

(10) Patent No.: US 10,441,001 B1
(45) Date of Patent: Oct. 15, 2019

(54) PELVIC RETAINER AND BODY CLAMP

(71) Applicant: Noel Edmonds Chase, Toronto (CA)

(72) Inventor: Noel Edmonds Chase, Toronto (CA)

( * ) Notice: Subject to any disclaimer, the term of this patent is extended or adjusted under 35 U.S.C. 154(b) by 0 days.

(21) Appl. No.: 16/248,837

(22) Filed: Jan. 16, 2019

(51) Int. Cl.
| | | |
|---|---|---|
| *A41B 9/00* | (2006.01) | |
| *A41D 7/00* | (2006.01) | |
| *A61F 13/14* | (2006.01) | |
| *A61H 39/04* | (2006.01) | |
| *A61F 13/00* | (2006.01) | |

(52) U.S. Cl.
CPC .............. *A41B 9/002* (2013.01); *A41D 7/005* (2013.01); *A61F 13/00051* (2013.01); *A61F 13/14* (2013.01); *A61H 39/04* (2013.01)

(58) Field of Classification Search
CPC ...... A61B 17/1325; A61B 2017/12004; A61B 17/132; A61B 17/1327; A41B 9/002; A61F 5/30; A61F 13/085; A61F 5/03; A61F 11/14; A61F 13/143; A61F 13/82; A61F 5/024; A61F 5/028; A61F 13/14; A61F 13/0051; Y10T 24/2187; Y10T 24/44; A41D 7/005; A61H 39/04

USPC .... 606/201, 203; 2/209, 400, 403, 406, 401; 128/846, 951, 96.1; 24/68 B
See application file for complete search history.

(56) References Cited

U.S. PATENT DOCUMENTS

2010/0299959 A1* 12/2010 Hammerslag ........ A43B 5/1666
36/50.5

* cited by examiner

*Primary Examiner* — Katherine M Shi

(57) ABSTRACT

The disclosed invention is a human body clamping device. In one significant fashion application as a pelvic retainer principally for female use, it facilitates an open-sided thong-like garment. Whereas all clothing garments that extends from the waist down (bottoms, pants, underpants, skirt, bathing suit bottoms, etc.) must currently wrap entirely around the waist in order to stay up, this invention allows fashion designers to design new styles of garments that allow the hips to be fully exposed. The novel clamping mechanism in this invention, combined with nano-grip fabrics and surfaces, ensures that the invention remains secured to the body. For medical and therapeutic applications, it provides controlled pressure on a body part.

18 Claims, 15 Drawing Sheets

Section A

Mid-Section
(Retainer in closed position)

Mid-Section
(Retainer in open position)

Mid-Section
(Retainer in closed position)

Mid-Section
(Retainer in open position)

Mid-Section
(Retainer in closed position)

Mid-Section
(Retainer in open position)

Detail Mid-Section
(Retainer in closed position)

Detail Mid-Section
(Retainer in open position)

Detail Mid-Section
(Retainer in closed position)

Detail Mid-Section
(Retainer in open position)

Slice Section B

Detail Mid-Section

Detail Mid-Section
(Open Position)

Detail Mid-Section
(Partially closed position)

Mid-Section
(Clamp in closed position)

Detail Section C

Mid-Section
(Clamp in open position)

PELVIC RETAINER AND BODY CLAMP

CROSS-REFERENCE TO RELATED APPLICATIONS

No cross-reference is made to other applications.

STATEMENT REGARDING FEDERALLY SPONSORED RESEARCH OF DEVELOPMENT

No Federal Government support was received in the development of this Invention.

SEQUENCE LISTING, TABLE, OR COMPUTER PROGRAM LISTING

No sequence listing, table, or computer program is attached or accompanies this Application.

FIELD OF THE INVENTION

This invention is a novel clamping device for fashion, medical and other applications. In one key fashion application, principally for female use, it allows lower-body garments to be open-sided at the waist and hips, and ensures such open-sided garments cannot be inadvertently removed. It is able to ensure that grip is maintained with the skin, particularly when nano-gripping surfaces and fabrics are incorporated into the finished product and is not reliant on either pressure sensitive adhesives or spring force to remain in position. This invention can also be adapted for male use. In medical, therapeutic and acupressure applications, it facilitates fast application, and subsequent fast removal, of controlled pressure on a specific area of the body while allowing the body to be readily moved or turned.

BACKGROUND OF THE INVENTION

No other product category in the market is more driven by change than fashion. Fashion designers and the fashion industry are obsessed with defining new looks and trends. In making the human body appear as an art form, fashion design lends itself to extremes. However, regardless of design or materials used, the garment must stay on the body.

In order for this invention to work in the described fashion use, some relevant aspects of the female human form require closer examination. The female waist located just above the iliac crest typically has the least circumference on the torso and is often used to support bottoms, skirts, thong-type bikinis, etc. Hip-hugging bottoms, which sit below the iliac crest, are able to stay up because the circumference just above the buttocks and hips is inherently smaller than the circumference at the point below where the buttocks and hips are largest. For women of normal body build with a flat abdomen, the depth of their body just above the buttocks yet below the iliac crest, is typically less than at the maximum depth at the mid-point of the buttocks. However, for women of slim build with negligible hips, the same cannot be said for the relative width of their body at these same points. The front and sides of the waist band on a hip-hugging lower-body garment then provides virtually no support to hold the garment up, other than to provide a means of joining these sections of the waist band section to the section over the buttocks.

The region at the bottom of the lumbar area and top of the sacral area, where the buttocks begins to project outward, are the skin's surfaces next to the gluteus medius, the top of the gluteus maximus, and the recessed or cleft area of the upper portion of the sacrum. These features are less pronounced on a female in a sitting or squatting position. During the action of changing from a standing to sitting position, the skin in these areas experiences virtually no local vertical movement. However, when pushed laterally in one direction, perhaps by ones fingers, the skin in these same areas will undergo a small localized movement. Similarly, other than for small localized movements when pushed laterally, the skin on the mons pubis (also known as mons venus and mons Veneris on females) also undergoes virtually no movement, either when bending or twisting the torso or during breathing. Also, the depth of the body between the mons pubis and the area just above the buttocks remains constant during these body motions. (This can be verified by placing the fingers of one hand on the mons pubis and the fingers of the other hand just above the buttocks, and rotating and bending one's body through a number of motions). When a woman is walking or running, the relative movement between the top of the buttocks must also be considered. The compressed gluteus maximus of the back leg displaces the top of that buttock slightly upward while the outstretch gluteus maximus of the forward leg allows the top of that buttock to displace slightly downward. Thus, except for displacements at the top of the buttocks by leg movement, no significant relative displacement occurs between the mons pubis, the bottom of the pelvis and the perineum, and the area just above the buttocks, as these surfaces are all adjacent to the large pelvic bone. Therefore, an external device which only contacts these areas of the pelvis would also experience only the relative vertical displacement of the two buttocks during leg movements. To minimize any movement of an external device due to the localized movement of the skin, the position of the device could be readily adjusted slightly upward, provided adequate grip is maintained to the skin.

When a woman wearing tight-fitting bottoms sits or squats down, the gluteus maximus muscles and gluteus medius elongate, putting tension on the fabric covering the buttocks. For bottoms made of non-elastomeric fabric, this tension causes the waist band of the bottom to be pulled down on the buttocks. Highly elastomeric fabrics inherently overcome this issue. Thong-type garments are not affected by this issue as they do not provide coverage of the buttocks.

When contemplating ways to grip or hold to skin, it is important to distinguish between the adhesive and non-adhesive methods. Reactive adhesives like cyanoacrylates can achieve a dangerously-strong adhesion to skin. High-tack pressure sensitive adhesives (PSAs) hold well to skin, as exhibited in their many medical applications requiring temporary adhesion, but are unnerving to remove and the adhesion rapidly deteriorates when the adhesive becomes contaminated after multiple uses. For the same reasons, clothing that is taped to the body has had little appeal. A device that relies solely on pressure sensitive adhesives or on the spring force a U-shaped spring member to remain on the body is too prone to being inadvertently or deliberately removed by someone or something else, leaving the user perilously exposed. Additionally, the spring force of a U-shaped spring member varies depending on the size of the body being contacted, often leading to excessive force being used to provide retention to the body. The preferred option is then to grip the skin using a non-adhesive method. A surface consisting of a series of miniature suction cups, molded in an elastomeric material, is one possible option. Alternatively, the skin can be gripped by generating a frictional force, a combination of contact force and friction co-efficient. The higher the friction co-efficient, the less contact force is required to achieve the same grip. In everyday exposure, skin can be dry, wet or oily from natural body oils, all of which impact the friction co-efficient. A marvelled occurrence in nature, the gecko's feet has provided the impetus for recent advances in nano-gripping surfaces produced in low-durometer elastomeric materials, which are now considered to provide some of the best non-adhesive gripping surfaces. This technology is used to provide, among other things, temporary grip of items to walls or the dashboard of cars. The most advanced nano-gripping surfaces for robot end effectors (end-of-arm-tooling) can provide an extremely good grip to a multitude of convex surfaces. Under load, these surfaces generate high "shear adhesion" to provide grip.

In the event of a laceration or medical intervention in the body, external pressure is used to restrict the flow of blood. This is typically done with hand pressure, external weights, or external gauze and adhesive tape. Being gravity based, the weights can only provide contact force when directly on top of the patient. Applying hand pressure is effective, but can rapidly become inconsistent and this ties up a first-responder from attending to other urgent needs. To be effective, the adhesive tape holding the gauze down must be under considerable tension on the skin, which then must be unnervingly torn off the skin when the gauze is removed. Therefore, a device to quickly apply a controlled pressure on a laceration, which can then be left unattended, and quickly removed, is desirable.

Viniegra (U.S. Pat. No. 2,534,934), Marbach (U.S. Pat. No. 3,339,208), Axman (U.S. Pat. No. 4,394,781), Leonard et al (U.S. Pat. Nos. 5,367,715 and 5,396,662), Crawford II (U.S. Pat. No. 5,467,482), Ruiter et al (U.S. Pat. No. 6,738,988) disclosed open-sided thong-type garments, all with a structure made of resilient spring wire formed in a U-shaped loop, and which are reliant on spring force to remain on the body. While perhaps useful in a stationary mode when tanning, they would all slip on the body during normal body movements and are extremely susceptible to being inadvertently removed. Additionally, all of the prior art based on spring wire designs failed to consider the actual cross-sectional profile of the bottom of the pelvis and the perineum, as it does not have the U-shape which these devices all show. Unsell (U.S. Pat. No. 5,347,657), Davis (U.S. Pat. No. 5,832,535), Osterrath (U.S. Pat. No. 6,173,449) disclosed genital-covering garments which are dependent on adhesive tape to remain on the body, and which would initially remain on the body better than the prior art based on spring wire. Davis recognizes that adhesive tapes are only suitable for single use, in that case for medical procedures. While also susceptible to inadvertent removal, failure of the adhesive tape would render the product useless. Flygstad (U.S. Pat. No. 4,727,585), Tool et al (U.S. Pat. No. 4,783,822), Hung (U.S. Pat. No. 5,035,005) and Woo et al (U.S. Pat. No. 6,611,963) are instructive on ear clamping devices with means to adjust the clamping force within the spring-type construction. They are all ultimately reliant on spring force to remain on the head and inadvertent removal is generally not a concern in that application.

Within the medical prior art, Porter et al (U.S. Pat. No. 8,048,009) disclosed a clamping device for therapeutic applications. Segal et al (U.S. Pat. No. 8,226,587) disclosed extensive variants of a pelvic anchor brace and spinal support which show the device originating in the center of lower back, with bands wrapping only part way around both sides of pelvis. The multitude of disclosed bands are all dependent on spring force to provide retention on the body, whether by spring wire, spring strips or articulating band segments each forced inward by individual springs.

Within other areas of the prior art, a number of non-encircling gripping devices require consideration. Hand-activated remote grabbing devices for changing light bulbs, picking up articles on the ground or for treating thrombosis, such as Barron (U.S. Pat. No. 6,223,628), Buzby et al (U.S. Pat. No. 8,500,180), Ludwig et al (U.S. Pat. No. 8,777,287) and Kovarik et al (U.S. Pat. No. 9,901,245) either have a hinging jaw or jaws that are forced to collapse while being pulled into a restriction. The purpose of the rigid or flexible shafts or tubes are only to house the means of conveyance of the mechanical movement to the distal grabber. The articulate segments of Kovarik et al are specifically designed to not bias in one particular direction when tension is applied to the wire, as that would be undesirable for their application. Foreman (U.S. Pat. No. 6,370,740) disclosed a non-encircling mechanical clamp for cylindrical objects, which is activated by having two rigid circular sections close from a center point through a pushing force and open through a pulling force. Additionally, the contact faces of common C-clamps and other styles of clamps often include self-aligning faces, comprises a ball trapped in a socket that, for deliberate reasons, prevents the clamp face from becoming detached. For the proposed applications of this invention, there is specific merit to have a detachable self-aligning face that will readily realigned during closure, which this invention discloses.

The field of robotics has seen sophisticated advancements in gripper, end effector and end-of-arm-tooling (EOAT) technology, including robotic "hands" having multiple fingers with multiple phalanges controlled by mechanical, servo-electrical or pneumatic means, which has some relevance to this invention. Rovetta et al (U.S. Pat. No. 4,351,553) disclosed a multi-purpose mechanical hand, consisting of three fingers having five rigid phalanges, each which have coil springs at the joints that cause the phalanges to normally spring straight, with gripping elements secured to the distal phalange of each finger. A tensioning cable is fixed to an arm extending inward on the distal phalange, and is slidably supported on a feature extending inward on each of the remaining phalanges, to where it is ultimately secured to an actuating device which applies or releases tension on the cable. A fashion product that passed through the perineum and between the buttocks, based on the concept of one of Rovetta et al's fingers, would clearly be extremely uncomfortable. Furthermore, with the support for the tensioning cable in the middle of each joint and independent springs at either end, these supports would be drawn together, digging in and pinching the skin as tension is applied on the cable. By have the tensioning cable attached on an inner lever arm on the last joint, the torsional movement of the gripper is inherently restricted, limiting its ability to self-align to the object being gripped. Smallridge (U.S. Pat. No. 5,029,646) disclosed another multi-phalange finger design but the tensioning cable is contained within the phalanges themselves and compression springs replace Rovetta et al's coil springs to provide a resilient opening means for the fingers. Dollar et al (U.S. Pat. No. 8,231,158) undertook a comprehensive examination of the prior art and industry advancements in robotic hands and fingers. Their disclosure, and that of Lin et al (U.S. Pat. No. 8,573,663) and later iRobot (U.S. Pat. No. 9,004,559) are all based on fingers with multiple rigid phalanges connected by hinging joints that are separate from the tensioning cable and are particularly not biased in the closing direction. These prior art focus on the issue of compliance within the robotic fingers and disclose alternative means to provide resilience at the hinging joints with the use of elastomeric materials. It is important to consider in these prior art that after tension has been applied on the cable to cause the robotic finger to grip an object, the phalanges and their hinging joints experience compressive forces which are trying to resist the fingers from opening. Such elastomeric joints would have insufficient flexural and compressive strength for the proposed applications in this invention. Robotic grippers comprising pneumatic multi-bellow actuators with integral nano-grip surfaces are widely considered to be the most compliant and versatile grippers now available, but which would also not be suitable for the proposed applications in this invention. McCarthy et al (U.S. Pat. No. 5,356,187) disclose a series of petals each comprising a resilient continuous strip, the thickness of which tapers continuously inward toward the distal ends. Longitudinal tensioning cables, originating both inboard and outboard at the base of each petal, are attached to the distal end of each petal, such that when tension is applied on either, the petals flex inward or outward. Cable guides are provided at limited points along each petal. Their invention is analogous with a fishing rod, which comprises a resilient tapered rod, with fishing line guided in eyelets below the rod to the hand-actuated reel. When a fisherman attempts to excessively reel the hook inward after it has caught on the distal eyelet, the rod bends toward the eyelets. Specific novel features of the invention now being disclosed go beyond the limitations of the "fishing rod" concept of Rovetta et al with its external tensioning cable, and allow the proposed fashion application to be properly addressed. McCarthy et al further disclose an optional hinging distal end of the petal, to which the tensioning cable is attached. The hinging end is positioned in the center with coil springs, and is allowed to travel to stops on either side of the hinge. This is similar to the distal phalange of Rovetta et al, with its external tensioning cable to activate a hinging end, and for the same reasons, would be completely unusable for the proposed fashion application.

SUMMARY OF THE INVENTION

An objective of this invention is to disclose a novel clamping means that provides a controllable contact force on the human body to ensure that grip is maintained on the skin. It provides fashion designers the means, when properly utilized, to develop garments which are open-sided at the waists and to contemplate other fashion applications including earmuffs, headphones, thong shoes and non-encircling tops, bras and belts. The specific refinements needed to design a marketable fashion product are left to those more capable.

Another objective of this invention is to disclose a simple body clamping device that can provide localized compression on the pelvis, chest, legs and other areas of the human body as required for medical or therapeutic use. Numerous other applications are possible where limited clamping or gripping is required, and the inventor leaves it to the reader to contemplate them.

This invention discloses multiple configurations of novel front and back sections, each which disclose different means to achieve similar functions. In order to reduce the overall number of figures, novel configurations of the front sections have been combined with novel configurations of the back section in the initial figures. Novel configurations of the back section only and configurations of a specific component are the sole focus in subsequent figures. It is evident that these novel front and back sections can be configured in any combination, all of which are part of the preferred embodiment of this invention. While this invention is a mechanical device, an electronic force gauge can be incorporated into a marketable product to monitor the force being applied by the clamp, and is part of the embodiment of this invention.

BRIEF DESCRIPTION OF THE DRAWINGS

In the drawings which illustrate the embodiments of the invention.

DETAILED DESCRIPTION OF THE INVENTION

Throughout the figures, some component designs appear in multiple configurations of the invention that are either identical to or are a small variant of a similar design, and have the same utility. Flexible components, such as cables and sheathing, which have been reshaped for each configuration and may only have a small, less obvious or less important variation in length, have been given common numbers throughout. This has been done to reduce the number of unique components and component numbers needed to depict the invention.

Figure 1:
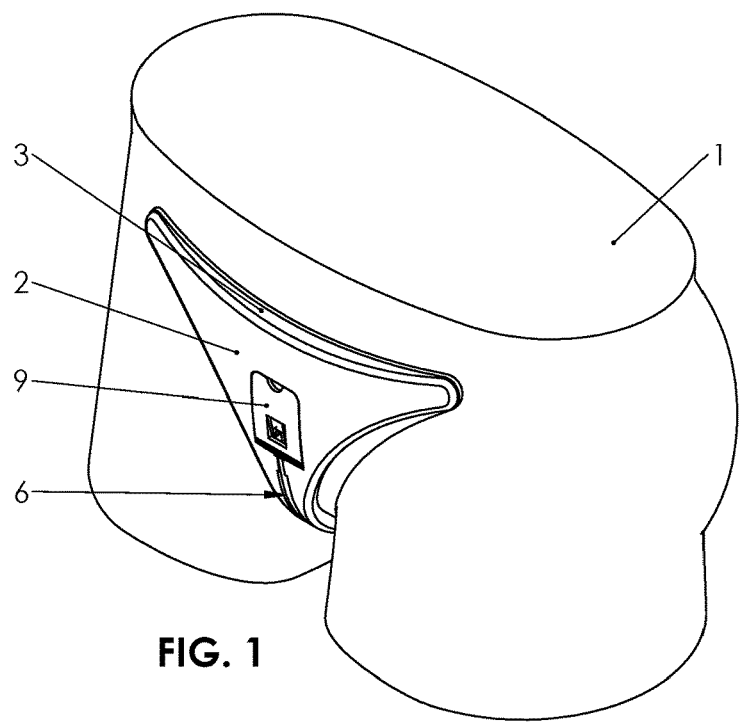
FIG. 1 is a front isometric view of the female pelvic region and a configuration of the pelvic retainer with a toggle latch on the front support and a fixed back support, in the closed position, showing the pelvic retainer contacting the pubic area, bottom of the pelvis, and above the buttocks.
Figure 2:
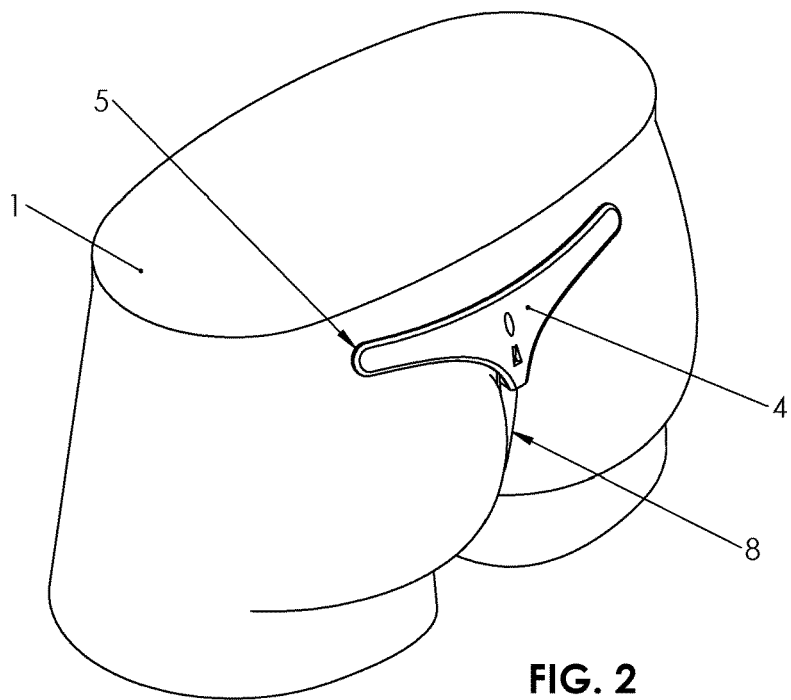
FIG. 2 is a rear isometric view of the same details in FIG. 1.

FIG. 1 and FIG. 2 show how the embodiment of this invention has been adapted as a pelvic retainer, how the pelvic retainer fits to the human female pelvis 1, with some components of one configuration of it shown. The pelvic retainer is the means to hold up lower-body garments without the need for the garment to wrap around the entire waist. It can be worn as is, as a thong-like bikini bottom. Alternatively, open-sided dresses, skirts, pants, shorts, leggings and other garments can be secured externally and internally to it, by means of hook-and-loop fasteners, clips, buttons or stitching. The particular configuration of pelvic retainer shown in these views has a toggled latch 9 on a toggle front support 2 and a fixed back support 4, the purpose of which will be described below and in subsequent paragraphs. The functionality of the fixed back support 4 is the most basic of the configurations being presented, and provides the least ability to adjust to the body or adapt to its movements. The toggle front support 2 forms the front face of the pelvic retainer and spreads the clamping force over the mons pubis and is substantially rigid, yet resilient to flex as necessary to conform to body. It sits below the abdomen, is contoured on the sides to provide clearance with the left and right groins and extends to the bottom of the pelvis. Front grip surface 3 directly contacts the mons pubis and the areas around it. Recent developments in hi-grip, and nano-grip surfaces for fabrics and molded items provide the most ideal grip to many surfaces, including skin. In order to achieve the best grip to the skin's surface, the pubic hairs of some areas of the mons pubis would ideally need to be shaved, which many women do when wearing a bikini bottom. As the front grip surface 3 is substantially flexible, it can extend into the groin, onto the abdomen and into the genital areas, if desired for functionality or fashion reasons. The fixed back support 4 provides the back face of the pelvic retainer and spreads the clamping force over the bottom of the lower back at the top of the buttocks and is also substantially rigid, yet resilient to flex as necessary to conform to body. The size and shape of fixed back support 4 is a balance of function and fashion. Similar to front grip surface 3, fixed back grip surface 5 is also made of a hi-grip fabric or elastomer and provides the gripping surface to the skin at the back. Although shown as matching the outline of the fixed back support 4, ostensibly to show a minimalistic design, fixed back grip surface 5 can provide much greater coverage of the buttocks, if desired. Fixed back tube 6 joins toggle front support 2 with fixed back support 4 through the perineum and passes around the bottom of the coccyx and between the buttocks. Fixed back tube 4 is made of a material that has suitable strength and resilience. It is important to note that the spring memory in fixed back tube 4 is not aiding in the closing force of the pelvic retainer, but is actually allowing it to spring and flex open. This is a key difference from all prior art for body-retaining items, including head phones, which uses the spring force to retain the device on the body. Cable 7 (not shown) passes internally through fixed back tube 6 and is made of a high-tensile strength material. Fixed back tube 6 is covered with tube cover 8, made of a suitable material to provide comfort and hygiene in the genital and anus areas and to minimize chafing with the buttocks during movement. Although shown tightly fitting on fixed back tube 6, tube cover 8 can be more loosely fitting. Toggle latch 9 on toggle front support 2 is used to apply and release tension on cable 7, the purpose of which will be explained in subsequent paragraphs.

Figure 3:
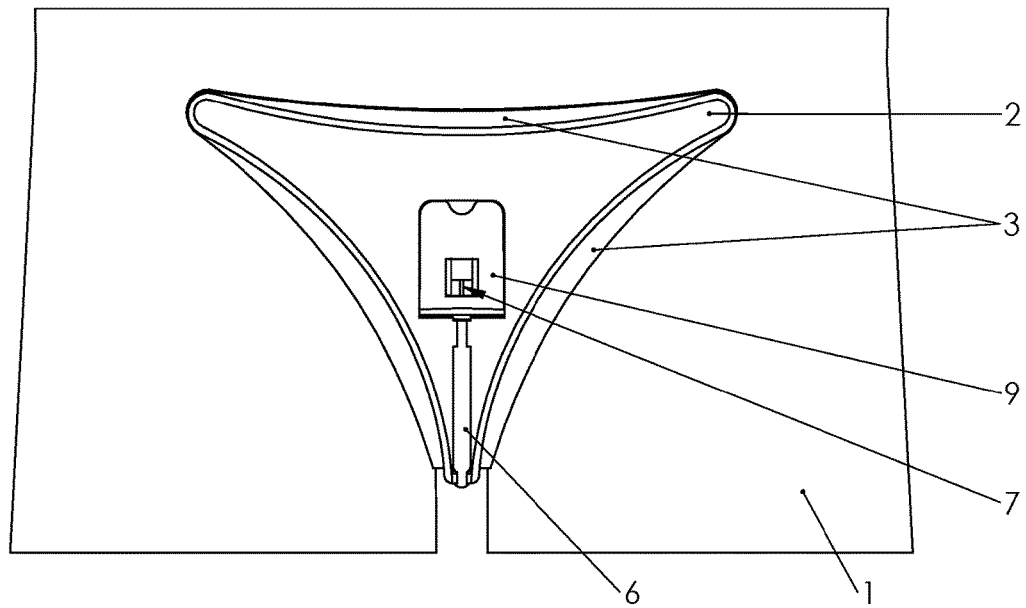
FIG. 3 is a front view of the same details in FIG. 1.
Figure 4:
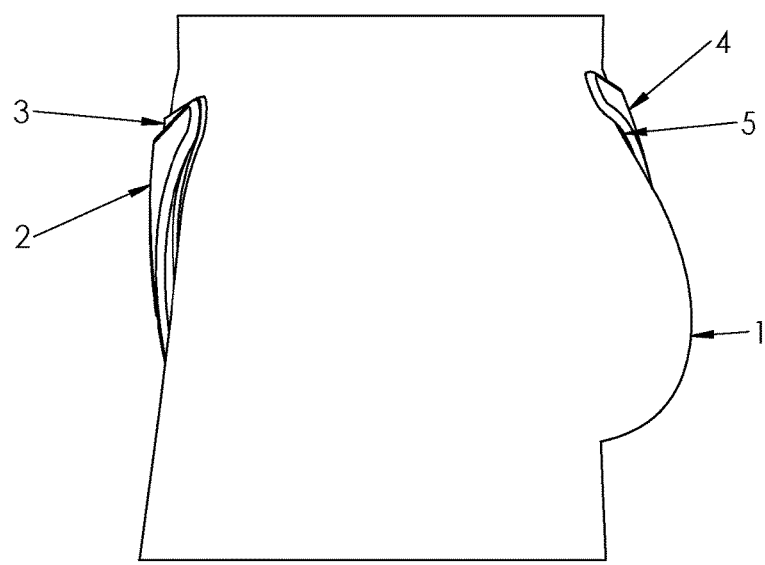
FIG. 4 is a side view of the same details in FIG. 1.

FIG. 3 and FIG. 4 show two addition views of the same configuration of pelvic retainer in FIGS. 1 and 2, with the same components identified. In the front view, the overall shapes of toggle front support 2 and front grip surface 3, and how they are positioned on the mons pubis, are shown. It is evident how the sides of the toggle front support 2 are set inward from the groin and from the outer edges of crotch to ensure that there is no interference with it during any leg movement. Toggle front support 2 extends down to the bottom of the pelvis to provide maximum support and alignment for fixed back tube 6. Fixed back tube 6 fits in a slot in toggle front support 2 which has retention features near the top of fixed back tube 6 and near its bottom as fixed back tube 6 exits from the slot, to securely position it during use. Toggle front support 2, with its front grip surface 3, can be readily separated from the combined assembly of fixed back support 4 with fixed back grip surface 5, fixed back tube 6, cable 7, tube cover 8, and toggle latch 9. This permits the pelvic retainer to be packaged in a much smaller size for shipping, and allows for easy interchangeability of different sizes, shapes and colors of toggle front support 2 and front grip surface 3. From the side view in FIG. 4, it is evident that fixed back support 4 sits just above the buttocks. Products intended to be fitted and worn on the human body require that they be supplied in multiple sizes or made adjustable, and it is evident that this invention will readily permit that.

Figure 5:
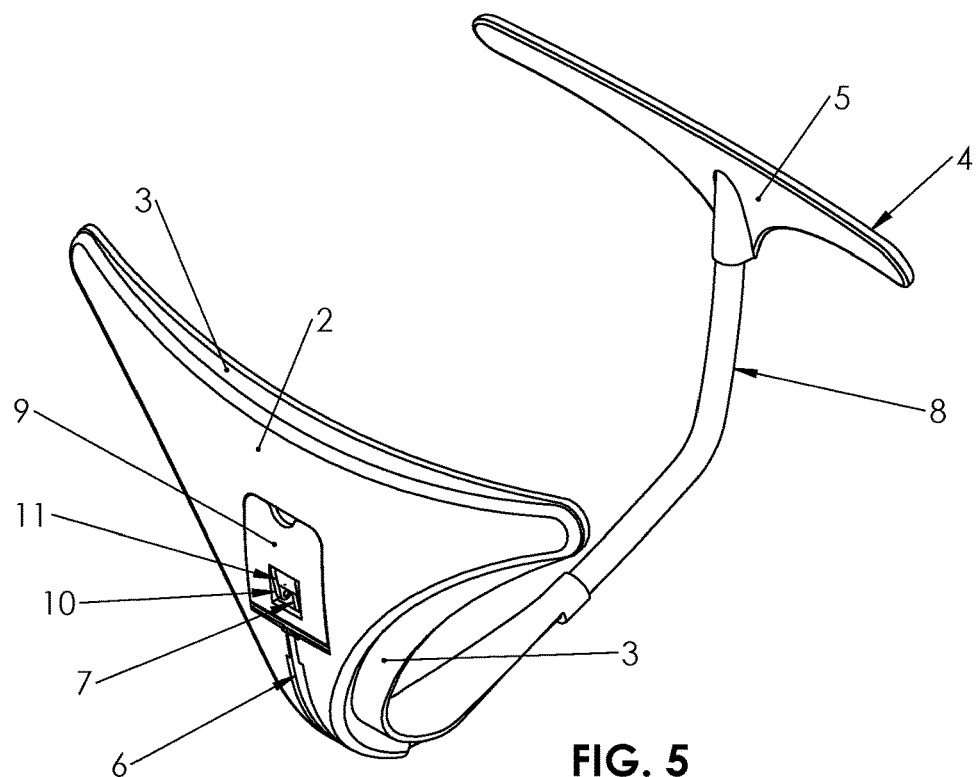
FIG. 5 is a front isometric view of the same configuration of pelvic retainer in FIG. 1.
Figure 6:
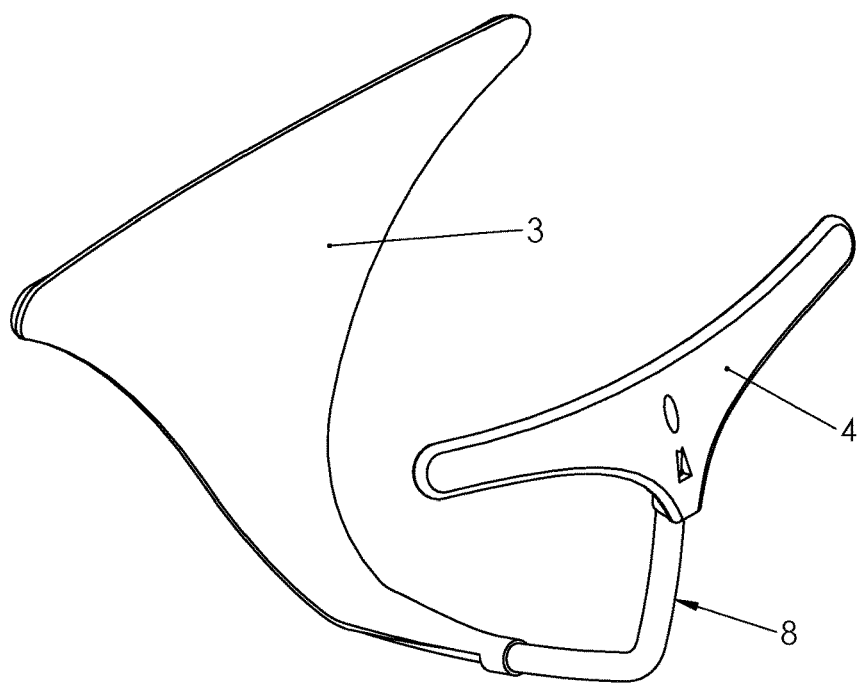
FIG. 6 is a rear isometric view of the same configuration of pelvic retainer in FIG. 1.

FIG. 5 and FIG. 6 show the pelvic retainer on its own, with the components identified previously now fully evident. The shape and contours of toggle front support 2 and fixed back support 4 can be seen. The respective front grip surface 3 and fixed back grip surface 5 are shown with similar contours, but are made of flexible materials which would readily conform to the skin's surface contours. Although front grip surface 3 is shown ending in the crotch and fixed back grip surface 5 being no larger than back support 4, both of these surfaces could be one continuous piece to provide more body coverage through the crotch and on the buttocks. Fixed back tube 6 is shown fitted in the slot which follows the contour of the lower half of toggle front support 2. Cable 7 is secured by a set screw (not shown) to toggle latch pin 11 which in turn is allowed to pivot at both ends on toggle latch arms 10, both of which pivot on toggle latch 9. The cable 7 passes through fixed back tube 6 and is fitted on the other end with a cable lug which seats in fixed back support 4. The purpose of having the cable tensioning device on the front support is for convenience only, as it allows the wearer to close the pelvic retainer from the front, much like zipping or buttoning up pants. Although the figures in this invention show the cable tensioning device to be on front support throughout, by no means must it be there, as it could alternatively be on the back support and the cable lug on the end of cable 7 would then be secured to the front support. Some designers may deem that having the cable tensioning device on the back support is more aesthetically appealing or practical for their design. Thus, both options of having the cable tensioning device on either the front or back support is deemed to be part of the preferred embodiment of this invention.

Figures 7, 8:
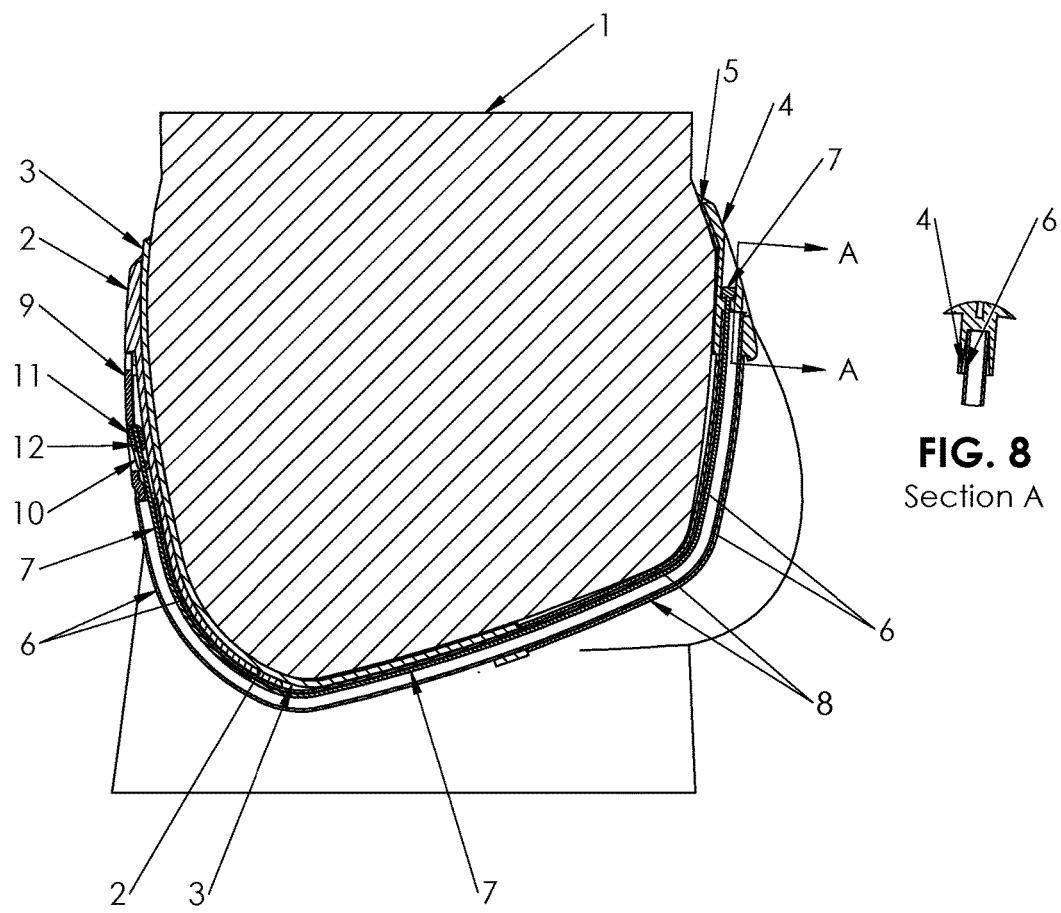
FIG. 7 is a mid-section view of the same configuration of pelvic retainer in FIG. 1.
FIG. 8 is detail section view A of the same configuration of pelvic retainer in FIG. 1.

FIG. 7 provides critical details of the pelvic retainer shown in the previous figures. This view highlights the general contours of the human female pelvis 1 through the mid-section. The bottom of the abdomen and the curvature of the mons pubis down to the bottom of the pelvis and genital area, are shown on the left. The skin next to the upper region of the sacrum, following down the sacrum and around the bottom of the coccyx and under the anus are shown at the right side. With the outline of the buttock shown behind, this view shows the critical difference in the depth of female form which allows this invention to work. It also shows the space provided between the buttocks next to the sacrum and coccyx where the back section of fixed back tube 6 with tube cover 8 are positioned. The bottom of the female pelvis and the perineum, including the genitals and anus, consists of soft tissue which generally forms an outward curvature that is inclined upward to the back, roughly following the incline from the bottom of the pubic symphysis to the bottom of the coccyx. Fixed back tube 6 follows the female profile in these areas, forming a continuous outward curvature over its entire length, albeit of varying radii. When the user is seated, a small clearance for fixed back tube 6 from the seating surface is provided by utilizing the clearance afforded by the pubic arch with the bottom of the ischial tuberosity and additional clearance provided by the fat and muscle tissue of the buttocks, and by having fixed back tube 6 push slightly upward on the soft tissue. A traditional closed-sided thong bikini functions similarly, albeit with a less rigid structure.

Further in FIG. 7, toggle front support 2 is shown in front of the mons pubis and extending down to the bottom of the pelvis. Front grip surface 3 is shown contacting these areas and providing optional additional coverage of the genital areas. Fixed back support 4 and fixed back grip surface 5 are shown generally above the buttocks, and also extending part way between the buttocks next to the sacrum. Fixed back tube 6 is inserted into a tapered hole in the bottom of fixed back support 4, and appropriately secured, in the figure shown with a flaring at the top which fits into a small opening in fixed back support 4. The back end of cable 7 has a lug which is retained by fixed back support 4. Cable 7 passes tightly along the inside curvature of fixed tube 6 to where it is secured to toggle latch pin 11 with set screw 12. The continuous outward curvature of fixed tube 6 ensures that this will certainly happen, although straight sections in fixed tube 6 are acceptable. Toggle latch pin 12 is connected to and able to rotate on the two toggle latch arms 10, which are in turn connected to and able to rotate on toggle latch 9. The circular bottom of toggle latch 9 is retained in a circular groove in toggle front support 2, which allows it to pivot. Toggle latch 9 is held closed by the cam action from the center of toggle latch pin 12 being slightly over-rotated with toggle latch arm 10. A secondary fastening means, such as a hook-and-loop fastener, can be fitted between toggle latch 9 and toggle front support 2 to provide a more secure closure. Toggle front support 2 is deliberately not permanently attached to toggle latch 9 nor fixed back tube 6, in order to allow it to be readily removed for storage or replacement. The action of opening and closing of toggle latch 9 correspondingly releases and applies tension on cable 7. By putting tension on cable 7, fixed back tube 6 bends inward, overcomes the outward spring force from its resilience. With the high-tensile strength cable 7 under tension tightly on the inner curvature of the fixed back tube 6 to resist the tensile load, and the outer extremities of fixed back tube 6 better able to resist compressive load, the outward flexing of fixed back tube 6 is substantially inhibited. Thereby, the controlled contact force of front grip surface 3 and fixed back grip surface 5 can be maintained. A detailed analysis of the longitudinal and lateral stresses within the tube can be done to optimize its cross-sectional profile and the most suitable materials for it. A co-extrusion of different materials or specific placement of oriented fiber reinforcements are possible. By changing the local wall thickness, shape and diameter of fixed back tube 6, the local stiffness can be varied along its length. This could allow, for instance, for greater flexibility in the back section of fixed back tube 6 while maintaining rigidity in the front and bottom sections. This issue is addressed in further detail in later figures. As a fashion product, a comfortable fit is important to achieve, which is highly subjective. Different sizes and shapes of fixed back tube 6 could be provided to accommodate different body sizes. It is also possible to readily make localized changes to the bend profile by means of simple tube bender, as part of the "fitting" process with a customer. FIG. 8 is a detail cross section through the center of fixed back tube 6, showing the tapered hole in fixed back support 4 where fixed back tube 6 is fitted. This taper allows fixed back support 4 to sway on the end of fixed back tube 6, in order to accommodate the differential vertical movement of the buttocks from leg movements.

Figure 9:
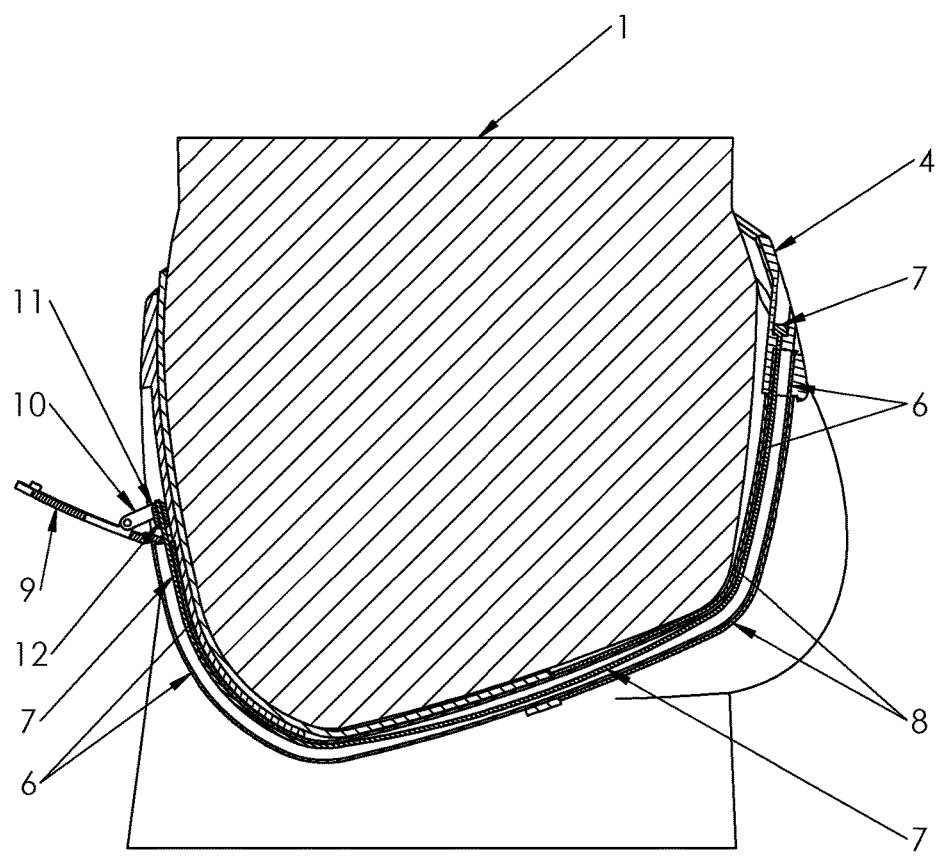
FIG. 9 is a mid-section view of the same configuration of pelvic retainer in FIG. 1, in the open position.

FIG. 9 shows all the same components as in FIG. 7, but with toggle latch 9 now in the open position and fixed back tube 6 sprung open, providing clearance for the pelvic retainer to be removed. Toggle latch pin 11 has dropped down to relieve tension on cable 7, which is shown loosely hanging inside fixed back tube 6. With the tension on cable 7 removed, fixed back tube 6 can be flexed slightly outward to aid in taking off and putting on the pelvic retainer.

Figure 10:
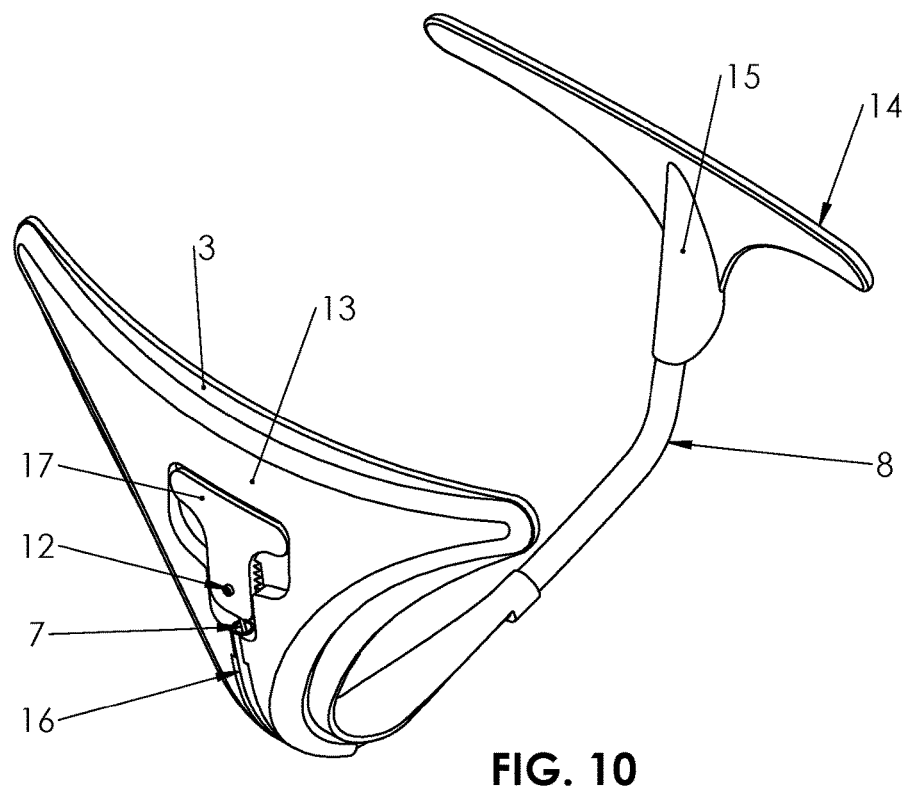
FIG. 10 is a front isometric view of a configuration of the pelvic retainer with a ratchet latch on the front support and a hinged back support, in the closed position.
Figure 11:
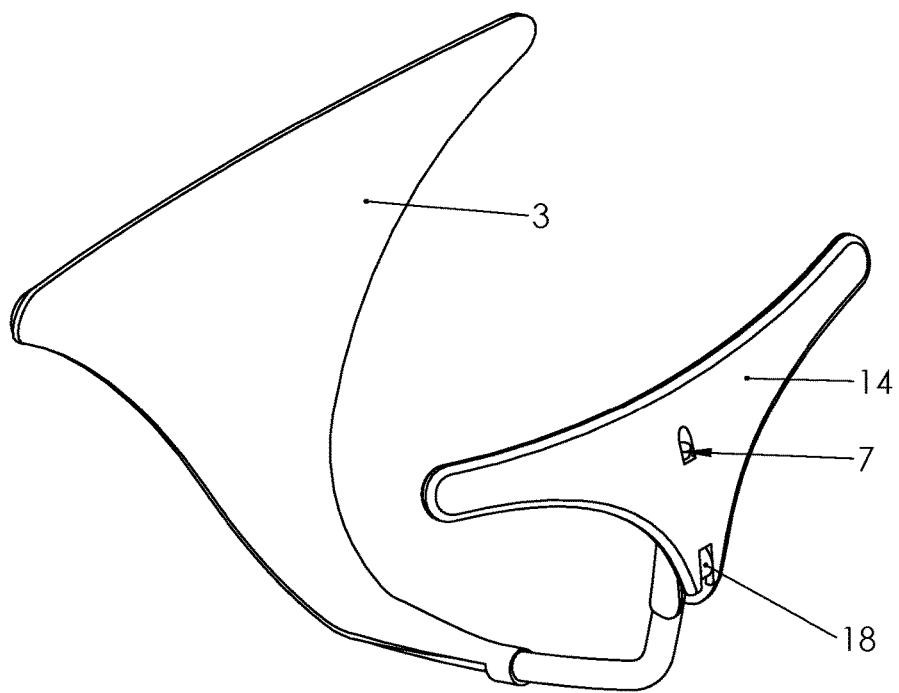
FIG. 11 is a rear isometric view of the same configuration of pelvic retainer in FIG. 10.

FIG. 10 and FIG. 11 show another configuration of front and back supports for the pelvic retainer, with tension on cable 7 now being applied and retained by means of a ratchet latch 17, and the clamping force for the pelvic retainer is applied by means of a hinging back support 14. Ratchet front support 13 provides the front face of the pelvic retainer and has a series of upwardly and outward sloping teeth that fit with a mating set of teeth on the inside of ratchet latch 17. Cable 7 is held to ratchet latch 17 by set screw 12. Hinged back tube 16 is fitted and retained in ratchet front support 13 in the same manner as previously described for fixed back tube 6 in toggle front support 2, with front grip surface 3 providing the gripping surface. The middle area of hinged back grip surface 15 conforms between the buttocks as hinged back support 14 is pivoted closed. Tube cover 8 covers the exposed areas of hinging back tube 16. Hinged support 18 supports hinge pin 19 (not shown) on which hinged back support 14 rotates. As with the previous configuration, ratchet front support 13 with front grip surface 3 can be readily detached from the other components for storage or replacement. While a hinged back support 14 is disclosed in these figures to allow the pelvic retainer to open and close, it is immediately evident that a hinge feature could be incorporated into the front support to achieve the same function. The front support could easily be split into and upper and low section, with the upper section being able to hinge outward to allow the pelvic retainer to be put on and removed. The latch mechanism could be incorporated into the upper hinged section, or alternatively into the back support. The option of having a hinged front support is part of the preferred embodiment of this invention.

Figure 12:
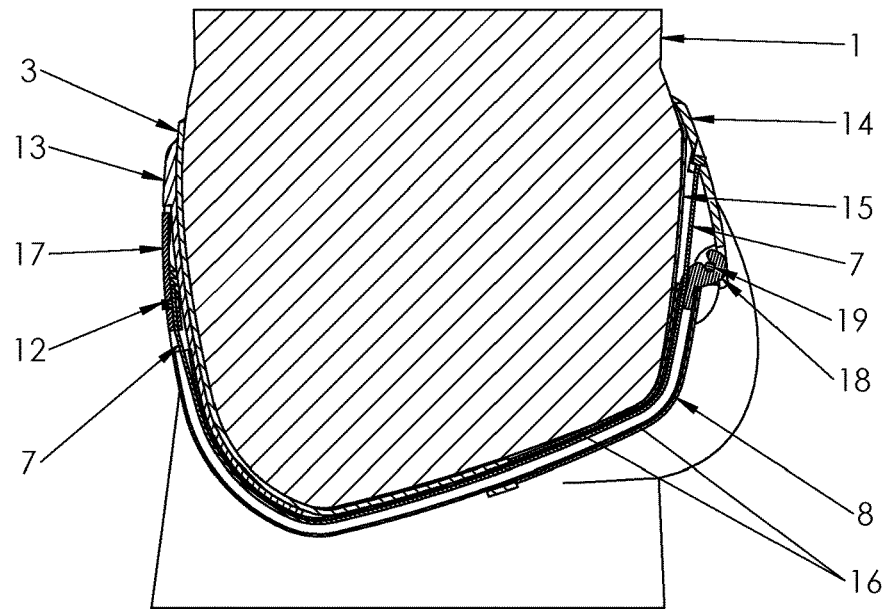
FIG. 12 is a mid-section view of the same configuration of pelvic retainer in FIG. 10.

The mid-section view in FIG. 12 show the complete details of the ratchet latch 17, hinged back support 14 and related components in their closed positions. The upwardly sloping teeth on ratchet front support 13 and mating teeth on ratchet latch 17 are now visible. Fixed incremental amounts of tension can be applied to cable 7 as ratchet latch 17 is ratcheted higher on ratchet front support 13, by means of the finger openings provided. A secondary fastening means, such as a hook-and-loop fastener, can be fitted between ratchet latch 17 and ratchet front support 2 to provide a more secure closure after being ratcheted. Cable 7 runs from ratchet latch 17, tightly along the inner radius of hinged back tube 16, through an inward slot in hinge support 18 to where it is retained in an opening in hinged back support 14 by the lug on the end. Front grip surface 3 provides grip, and tube cover 8 covers exposed portions of hinged back tube 16. Hinge pin 19 is fitted through hinged back support 14, and rests on hinge support 18. Because cable 7 is forward of hinge pin 19, hinged back support 14 is forced to rotate forward as tension is applied. Furthermore, with cable 7 running tight on the inner radius of hinged back tube 16 when tension is applied, hinged back tube 16 cannot flex outward at the back. This ensure the pelvic retainer remains closed. Hinged back grip surface 15 contacts the skin and also protects cable 7 from directly contacting the body. Because the clamping force is generated by a hinged mechanism, it is evident that more clamping force is generated toward the upper region of the hinged back support 14 than the lower portion. Whether more or less desirable, this would come down to user preference when considering the other options being presented. Other linear or rotary (dial) ratchet tensioning devices, that are commonly used on cycling shoes, snowboards bindings and in numerous other applications, can be used to provide incremental tensioning on cable 7, or replace cable 7 and directly connect to hinged back support 14, provided the direct connection means is of high tensile strength. These options are all part of the preferred embodiment of this invention.

Figure 13:
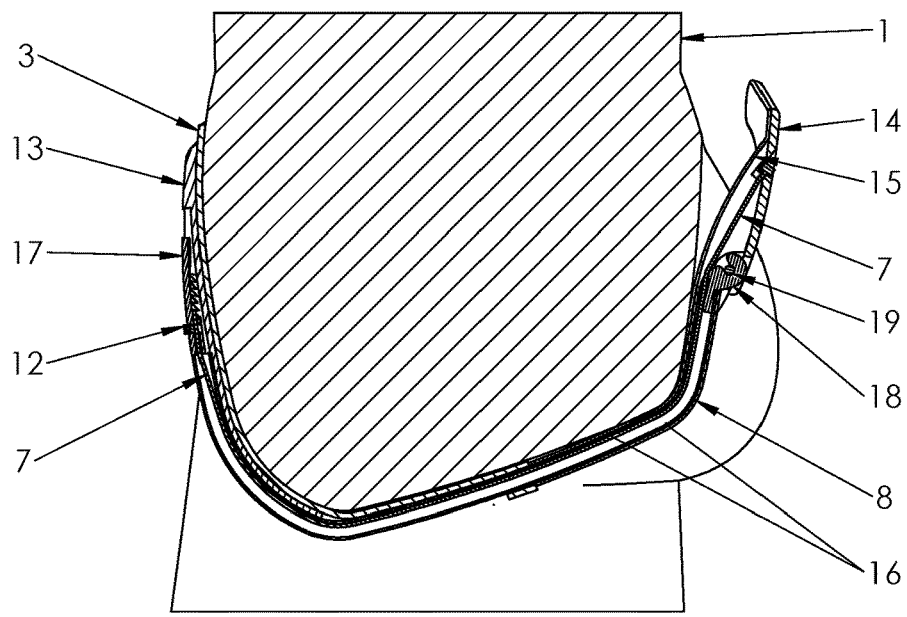
FIG. 13 is a mid-section view of the same configuration of pelvic retainer in FIG. 10, in the open position.

In FIG. 13, the same components are now shown in the open position. Ratchet latch 17 is in its lowest position, next to hinged back tube 16 and tension is released on cable 7. Hinged back support 14 can rotate open on hinge support 18 about hinge pin 19. The inward facing slot in hinge support 18 forces cable 7 toward the inner curvature of hinged back tube 16 while hinged back support 14 is in the open position. This eccentric positioning of the cable 7 ensures that when tension is applied, hinged back support 14 will always rotate forward. Hinge support 18 is shown with an upward facing slot. Either an open or closed slot can be provided, the purpose of which is to allow hinged back support 14 to sway to accommodate the differential movement of the buttocks from leg movements.

Figure 14:
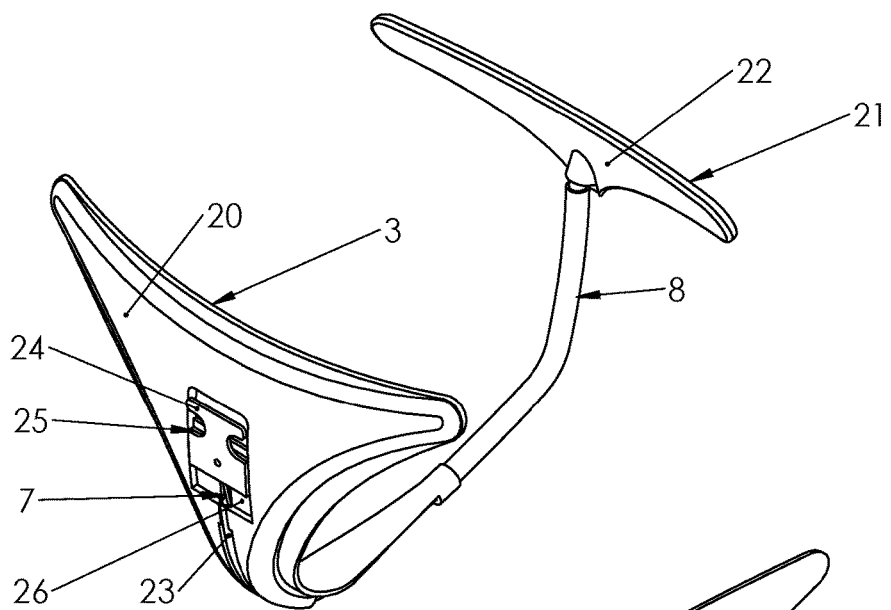
FIG. 14 is a front isometric view of a configuration of the pelvic retainer with a hook-and-loop latch on the front support and a sliding back support, in the closed position.
Figure 15:
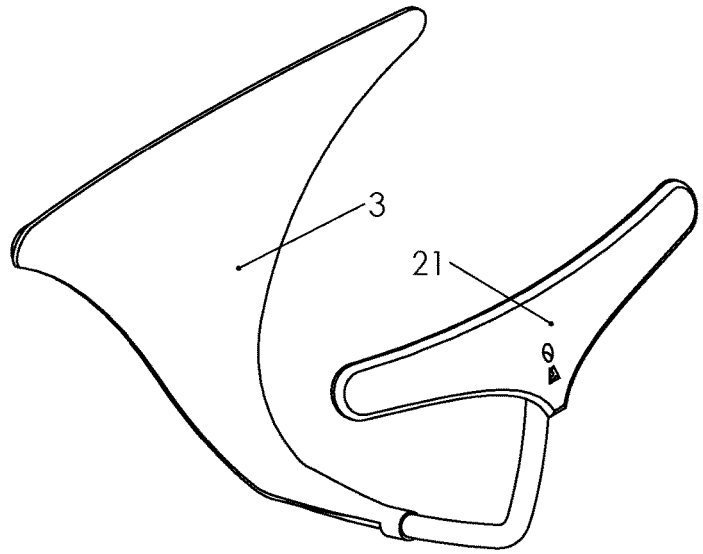
FIG. 15 is a rear isometric view of the same configuration of pelvic retainer in FIG. 14.
Figure 16:
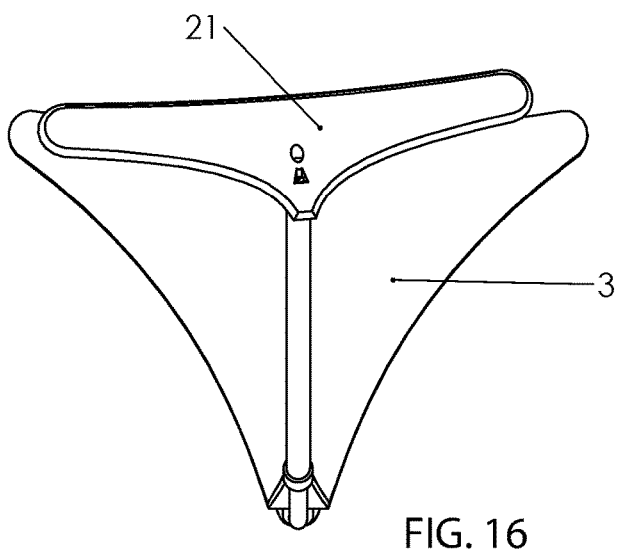
FIG. 16 is a rear view of the same configuration of pelvic retainer in FIG. 14, showing the sliding back support rotated slightly.

In FIG. 14 and FIG. 15, another configuration of front and back supports for the pelvic clamp are presented. In this configuration, tension is applied and released on cable 7 by upward and downward movement of hook-and-loop latch 24, with the finger slots provided. Although the movement is similar to that of ratchet latch 17 described previously, the tension can be applied with infinite control instead of fixed incremental amounts. Hook-and-loop latch 24 is fitting on the inside with latch hook-and-loop 25, which fastens to hook-and-loop 26 on hook-and-loop front support 20, the front face of the pelvic retainer. Sliding back support 21 provides the back face of the pelvic retainer and as fitted with sliding back grip surface 22. Cable 7 is fastened to hook-and-loop latch 24 by set-screw 12 (not shown) and extends through sliding back tube 23 to where it is held by its cable lug to sliding back support 21. As with the other configurations presented, sliding back tube 23 fits and is retained by hook-and-loop front support 20, and the latter with front grip surface 3 can be readily detached for storage or replacement. Front grip surface 3 and tube cover 8 perform the same purpose as with previous configurations. A small portion of sliding back tube 23, which mates with sliding back support 21, is bent outward. As shown in FIG. 16, sliding back support 21 is able to rotate on this angular axis to accommodate the differential movement of the buttocks from leg movements.

Figure 17:
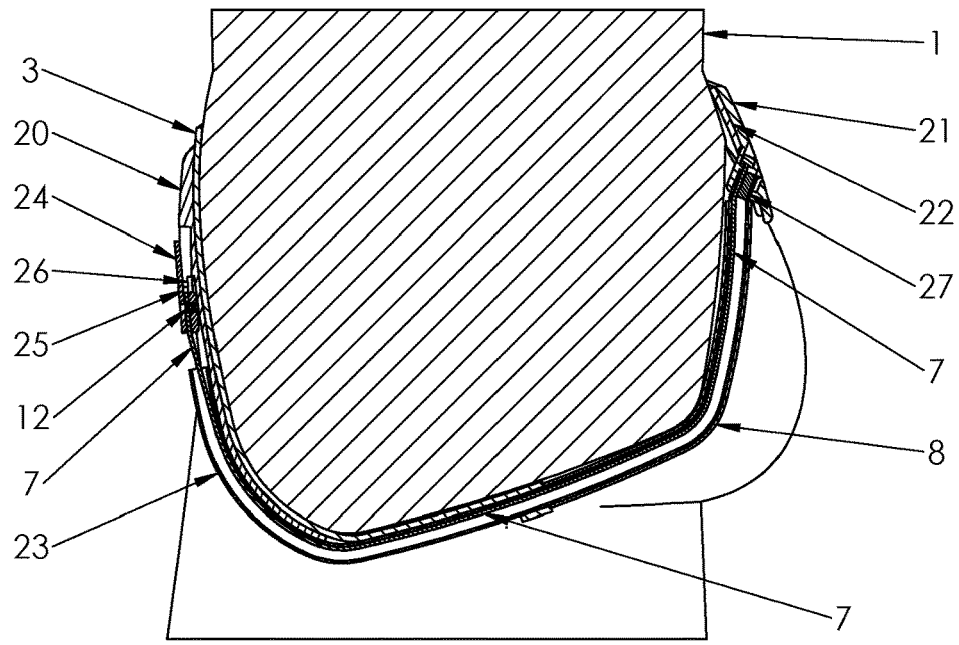
FIG. 17 is a mid-section view of the same configuration of pelvic retainer in FIG. 14.

The mid-section view in FIG. 17 shows the complete details of the hook-and-loop latch 24, sliding back support 21 and related components in their closed positions. Hook-and-loop front support 20 is shown in front of the mons pubis with the front grip surface 3. Hook-and-loop latch 24 is secured to cable 7 by set-screw 12 and is fitted with latch hook-and-loop 25, that fasten to hook-and-loop 26 on hook-and-loop front support 20. Sliding back tube 23 is fitted and retained on hook-and-loop front support 20 similar to previous configurations. The outward bend at the back of sliding back tube 23 is now evident. To ensure that cable 7 remains tight to the inner radius of sliding back tube 23 in the back section and as it bends outward, tube insert 27 is fitted into this section. Sliding back support 21 is able to slide inward and outward and rotate on the angled portion of sliding back tube 23. The inward and outward movement of sliding back support 21 facilitates removal of the pelvic retainer, as is evident in FIG. 18, and also accommodates the variations in body profiles of different users. The particular angle at the end of sliding back tube 23 allows sliding back support 21 to rotate on a suitable axis to accommodate the differential upward and downward displacement of the buttocks during leg movements. Sliding back support 21 is prevented from becoming completely detached by a retention feature at the end of sliding back tube 23, shown here as a small flaring. A longitudinal slot in sliding back support 21, which is closed at the bottom, accommodates the longitudinal movement of the retention feature, but limits its angular rotation to only what is necessary. It is readily evident that a separate component can provide the outward bend at the end of sliding back tube 23 and incorporate the requirements of tube insert 27 into it, like the separate hinge support 18 previous described. Both options are part of the embodiment of this invention.

Figure 18:
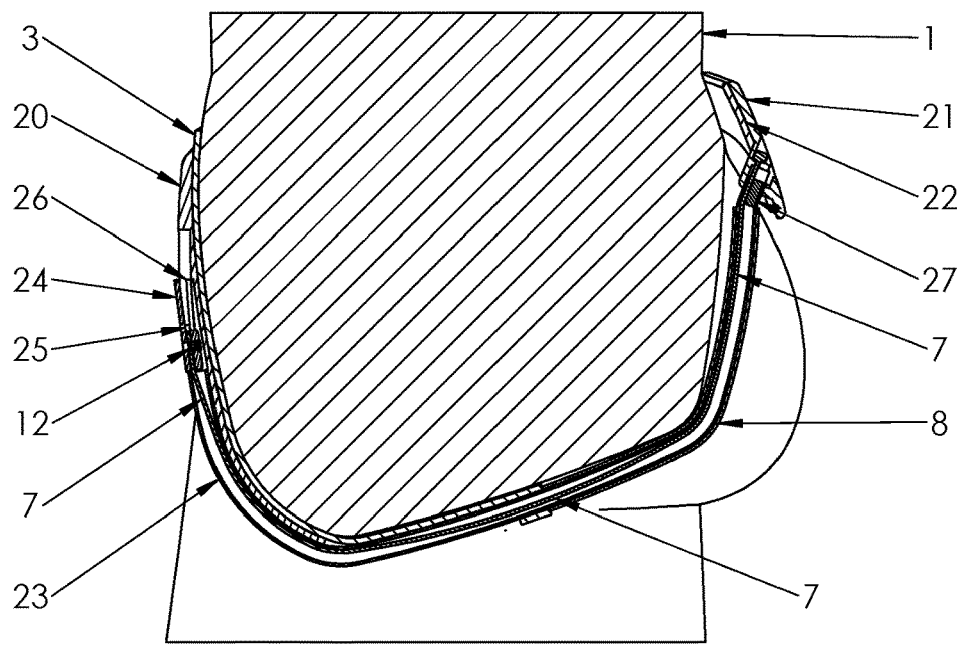
FIG. 18 is a mid-section view of the same configuration of pelvic retainer in FIG. 14, in the open position.

In FIG. 18, the same components are now shown in the open position. Hook-and-loop latch 24 is in its lowest position, next to sliding back tube 23 and tension is released on cable 7. Sliding back support 21 has slid outward on sliding back tube 23, and additional clearance is provided with sliding back tube 23 being sprung slightly outward.

Figure 19:
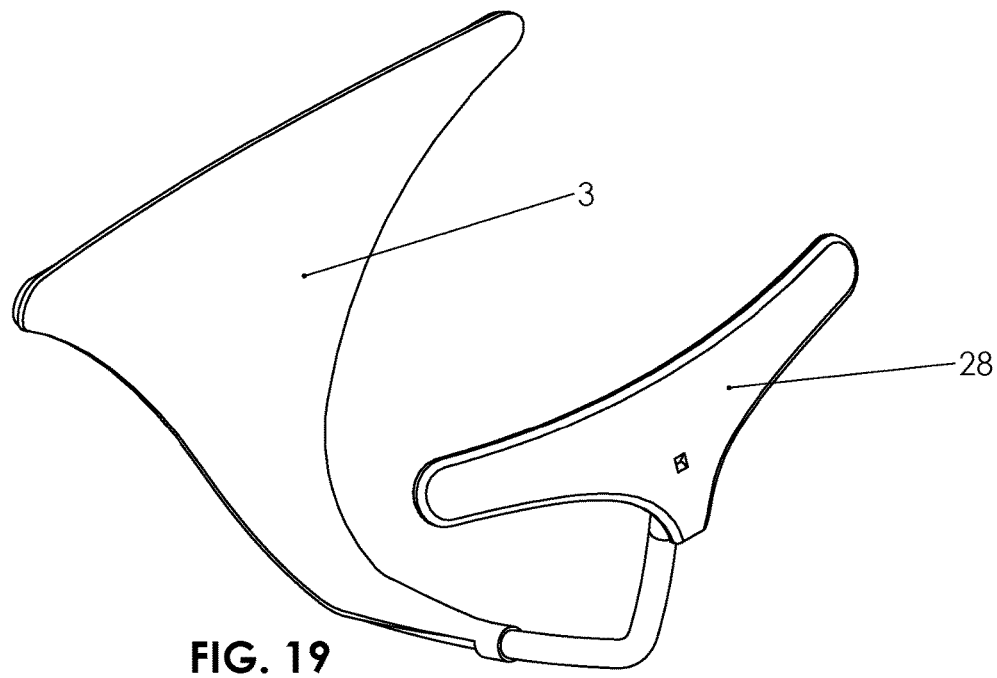
FIG. 19 is a rear isometric view of a configuration of the pelvic retainer with an internal self-aligning back support, in the closed position.
Figure 20:
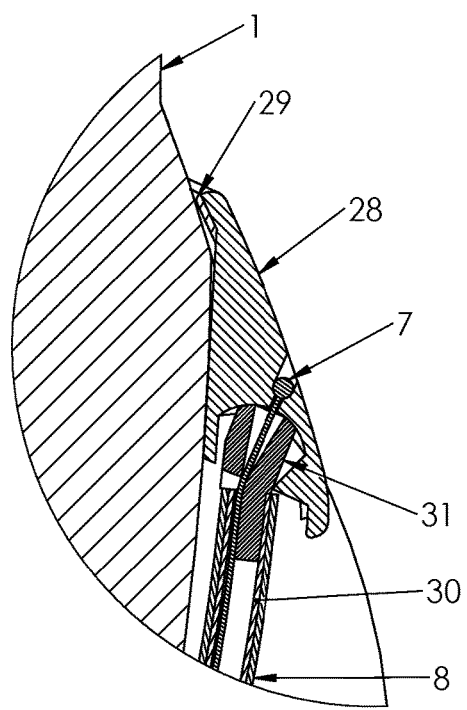
FIG. 20 is a detail mid-section view of the same configuration of pelvic retainer in FIG. 19.
Figure 21:
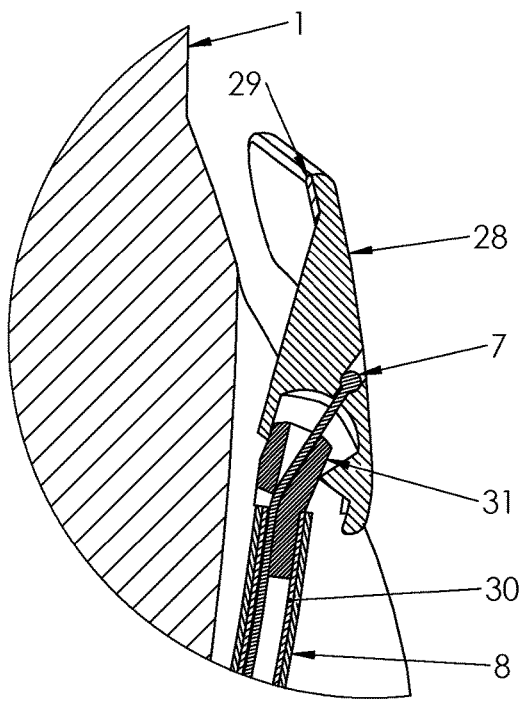
FIG. 21 is a detail mid-section view of the same configuration of pelvic retainer in FIG. 19, in the open position.

In FIG. 19, another configuration of the pelvic retainer is shown, with new material being introduced regarding the back section only. The rear isometric view shows the internal self-aligning back support 28, which is able to align itself to different user body profiles. The lug on the end of cable 7 is visible, as is tube cover 8. Detail mid-section view FIG. 20 shows the internal self-aligning back support 28 with its grip surface 29 in the closed position. Internal self-aligning back support 28 has an inward-facing tapered blind hole with a concave spherical bottom. Internal self-aligning tube fitting 31 is fitted to the back end of internal self-aligning back tube 30, angles outward from the tube axis and has a convex spherical end that matches the spherical radius of internal self-aligning back support 28. Internal self-aligning tube fitting 31 has an outward-facing tapered hole through the center of the angled portion, which joins an inward facing slot in the section that is inserted into the end of internal self-aligning back tube 30. Cable 7, with its lug seated in internal self-aligning back support 28, passes through the hole in the concave spherical radius in internal self-aligning back support 28, continues through the tapered hole in internal self-aligning tube fitting 31 into an inward-facing slot where it is forced against the inside radius of internal self-aligning back tube 30. The clearances provided between the tapered hole in internal self-aligning tube fitting 31 and cable 7, and between the outside of internal self-aligning tube fitting 31 and the outward tapered hole in internal self-aligning back support 28, allows internal self-aligning back support 28 to adequately pivot unobstructedly on its spherical radius. Although possible, it is generally not required to have internal self-aligning back support 28 pivot side-to-side in order to accommodate differential movements of the buttocks, as this is already dealt with through the angle on internal self-aligning tube fitting 31 acting similarly to the bend in the end of sliding back tube 23. Tube cover 8 provides a protective cover over internal self-aligning back tube 30. Detail mid-section view FIG. 21 shows internal self-aligning back support 28 with its grip surface 29 now in the open position, with the tension on cable 7 having been released. Guided by the outer sides of internal self-aligning tube fitting 31, internal self-aligning back support 28 is able to release contact of the spherical radius and slide along its tapered hole to provide additional clearance for the pelvic retainer to be removed. A means to prevent internal self-aligning back support 28 from becoming completely disengaged from internal self-aligning tube fitting 31 can be provided. A conventional "ball and socket" design could also be readily incorporated into internal self-aligning back support 28 and internal self-aligning tube fitting 31, in which the mating spherical surfaces always remain in contact, but the pelvic retainer could not be opened to the same extent.

Figure 22:
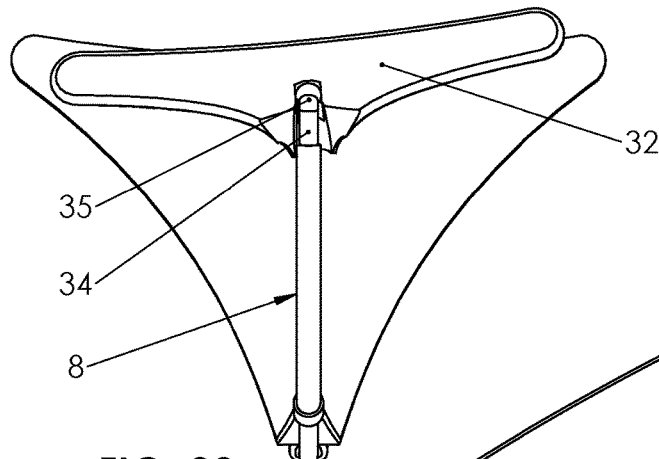
FIG. 22 is a rear isometric view of a configuration of the pelvic retainer with an external self-aligning back support, in the closed position.
Figure 23:
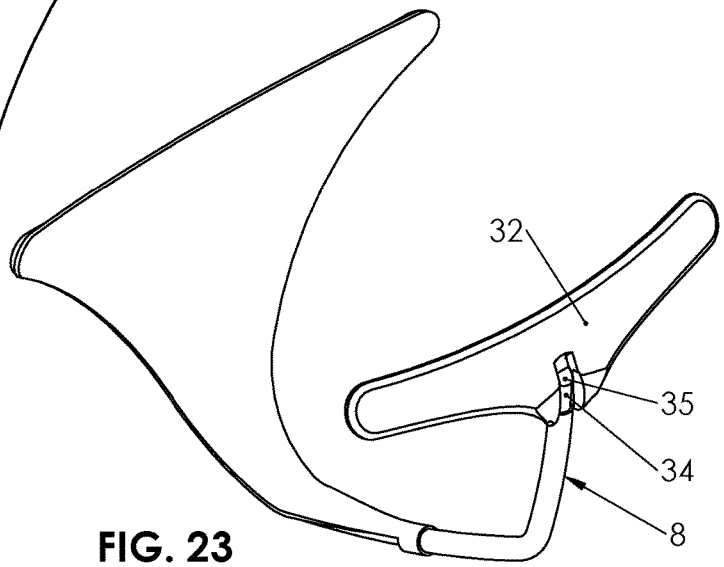
FIG. 23 a rear view of the same configuration of pelvic retainer in FIG. 22, with the external self-aligning back support rotated slightly.
Figure 24:
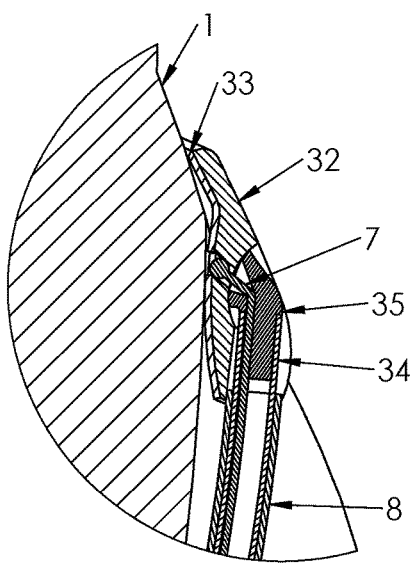
FIG. 24 is a detail mid-section view of the same configuration of pelvic retainer in FIG. 22.
Figure 25:
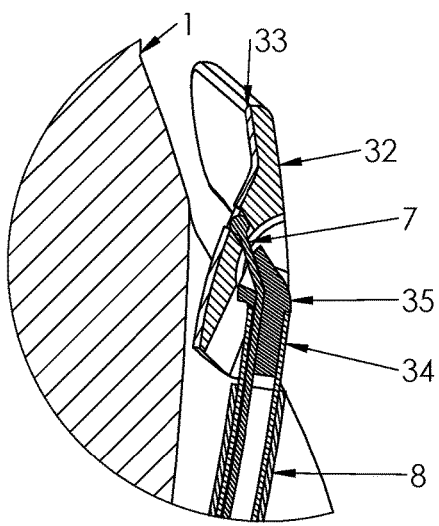
FIG. 25 is a detail mid-section view of the same configuration of pelvic retainer in FIG. 22, in the open position.

In FIG. 22, another configuration of the pelvic retainer is shown, again with new material being introduced regarding the back section only. The rear isometric view shows the external self-aligning back support 32, which is able to align itself to different user body profiles. The top section of external self-aligning back tube 34 and external self-aligning tube fitting 35 are visible above tube cover 8. In FIG. 23, external self-aligning back support 32 is shown slightly rotated to indicate how it accommodates the differential movement of the buttocks. This is possible because of the angular clearance on the sides of the slot in external self-aligning back support 32 to allow for the angular movement of external self-aligning back tube 34, as seen in this view. Detail mid-section view FIG. 24 shows the external self-aligning back support 32 with its grip surface 33, in the closed position. External self-aligning back support 32 has an outward-facing slot with a concave spherical bottom. External self-aligning tube fitting 35 is fitted to the back end of external self-aligning back tube 34, angles inward from the tube axis and has a convex spherical end that matches the spherical radius of external self-aligning back support 32. External self-aligning tube fitting 35 has an inward-facing tapered hole through the center of the inward-angled portion, which joins an inward-facing slot in the section that is inserted into the end of external self-aligning back tube 34. Cable 7, with its lug seated in external self-aligning back support 32, passes through the hole in the concave spherical radius in external self-aligning back support 32, continues through the tapered hole in external self-aligning tube fitting 35 into an inward-facing slot where it is forced against the inside radius of external self-aligning back tube 34. The clearances provided between the tapered hole in external self-aligning tube fitting 35 and cable 7, and between the outside of external self-aligning tube fitting 35 and the outward tapered hole in external self-aligning back support 32, allows external self-aligning back support 32 to adequately pivot unobstructedly on its spherical radius. Although possible, it is generally not required to have external self-aligning back support 32 pivot side-to-side, in order to accommodate differential movements of the buttocks, as this is already dealt with through the angle on external self-aligning tube fitting 35 acting similarly to the bend in the end of sliding back tube 23. Tube cover 8 provides a protective cover over external self-aligning back tube 34. Detail mid-section view FIG. 25 shows external self-aligning back support 32 with its grip surface 33 now in the open position, with the tension on cable 7 having been released. Guided by the outside of external self-aligning tube fitting 35, external self-aligning back support 32 is able to release contact pressure on it spherical radius and rotate in its slot, to provide clearance for the pelvic retainer to be removed. Although not shown, a means to prevent external self-aligning back support 32 from becoming completely disengaged from external self-aligning tube fitting 35, can be provided. A conventional "ball and socket" design could also be incorporated into external self-aligning back support 32 and external self-aligning tube fitting 35, in which the mating spherical surfaces always remain in contact, but the pelvic retainer could not be opened to the same extent. With the internal and external self-aligning features having now been disclosed, it is readily apparent that a self-aligning feature can be incorporated into the hinged back support 14 previously disclosed, and this option is part of the preferred embodiment of this invention.

Figure 26:
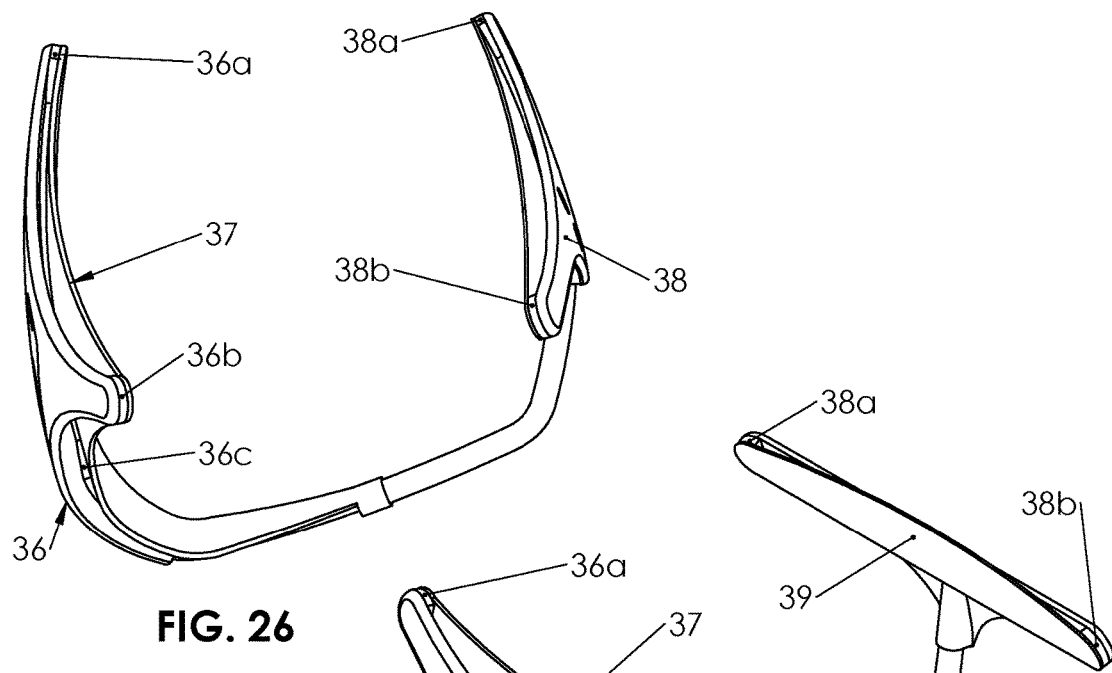
FIG. 26 is a perspective view of any of the configurations of pelvic retainers disclosed in the previous figures, but with the front and back grip surfaces secured at limited locations.
Figure 27:
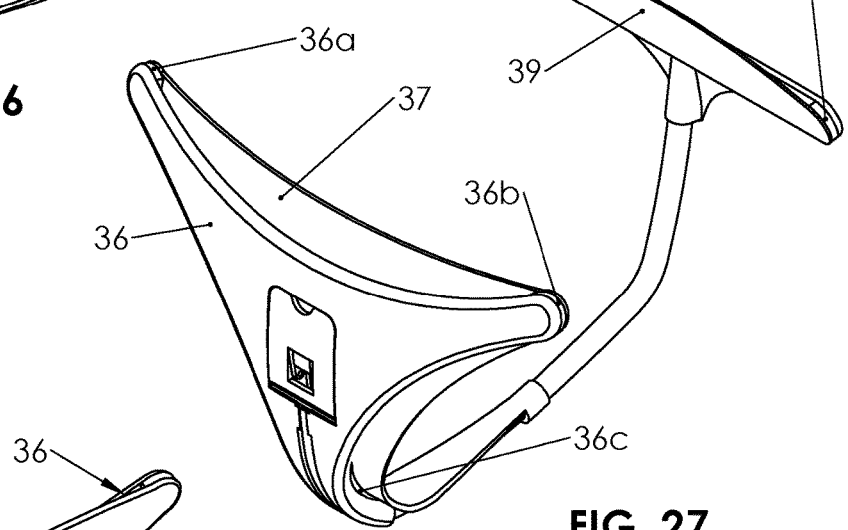
FIG. 27 is a front isometric view of the same configuration of pelvic retainer in FIG. 26.
Figure 28:
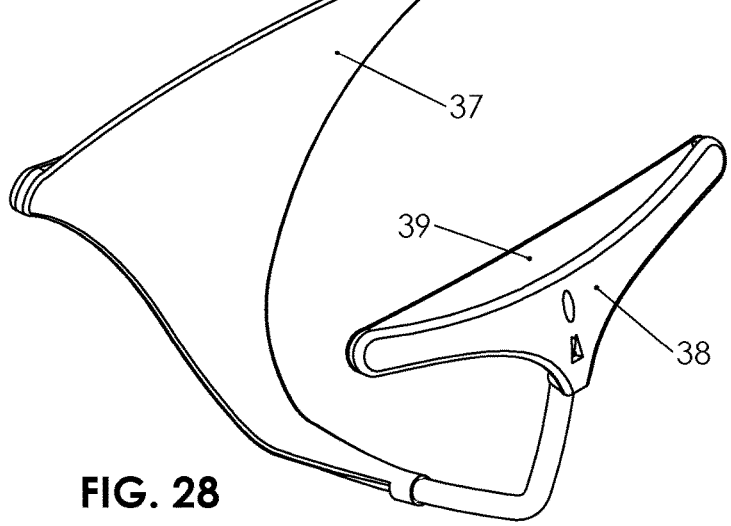
FIG. 28 is a rear isometric view of the same configuration of pelvic retainer in FIG. 26.

In FIG. 26, FIG. 27 and FIG. 28, a configuration of the pelvic retainer presented in the previous figures is used to disclose new material regarding a variation on where the front and back grip surfaces can be secured to their respective front and back supports, and only the new material has been identified. Front support 36 includes stand-offs 36a and 36b near the upper two ends and 36c in the middle near the bottom. Front grip surface 37 is only secured to front support 36 at the three stand-offs 36a, 36b and 36c, largely resulting in a gap between these two components and allowing them two function somewhat independently. One advantage is that front grip surface 37 can better conform to the variations in the mons pubis and crotch of different women, without being constrained by the more rigid front support 36, thus providing a better and more comfortable contact. The middle of front grip surface 37 can also be pulled up on the pelvic area independently of front support 36. As mentioned previously, nano-grip surfaces produce "shear adhesion" when put under shear load. In order to induce a shear load, this infers that front grip surface 37 should specifically be forced to stretch slightly when contacting the body. Commercially-available nano-grip surfaces, used to grip cell phones to dash boards and the like, are able to produce a similar grip on both sides. The back side of front grip surface 37 would inevitably make contact with the back side of front support 36 and the options exists to have the two surfaces either grip each other or slide on each other, both of which are part of the embodiment of this invention. Back support 38 has stand-offs 38a and 38b at both ends, to which back grip surface 39 is secured, largely resulting in a gap between the two of them, the purpose being the same as just described. Back grip surface 39 is specifically not shown to be additionally secured in the bottom middle, like front grip surface 37, in order to disclose this option. One advantage of not securing the grip surfaces in the middle is that a more uniform shear-load can be applied to the nano-grip surface in the vertical direction. Either option for both the front and back grip surfaces is part of the embodiment of this invention. As such, the front grip surface 37 is not required to extend fully to the bottom of the pelvis into the perineum.

Figure 29:
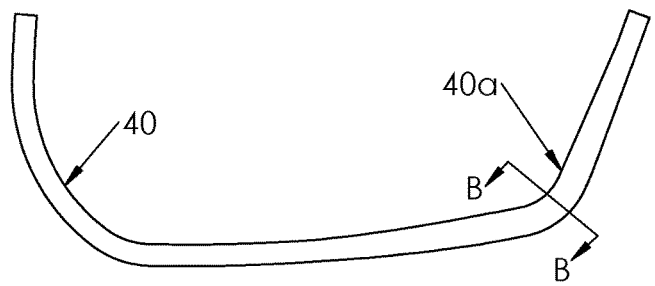
FIG. 29 is a side view of a tapered tube.
Figure 30:
FIG. 30 a slice section view B of the tapered tube in FIG. 29.

In FIG. 29 and FIG. 30, tube 40 is shown to have an elliptical profile in the region where it passes between the buttocks, as indicated by 40a. The purpose of this is to reduce the feel of the tube between the buttocks that could be evident during prolonged physical activity or from prolonged use of the pelvic retainer. Localized changes in the tube profile, from round to substantially elliptical, triangular, and square or any other geometric shape, can also be made to change its local stiffness, and are all part of the preferred embodiment of this invention.

Figure 32:
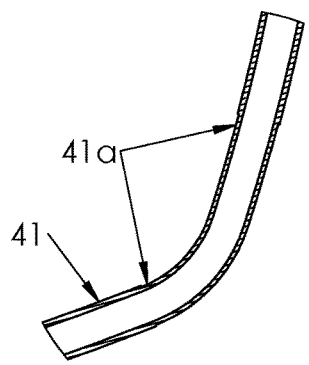
FIG. 32 is a detail mid-section view of the tube in FIG. 31.
Figure 31:
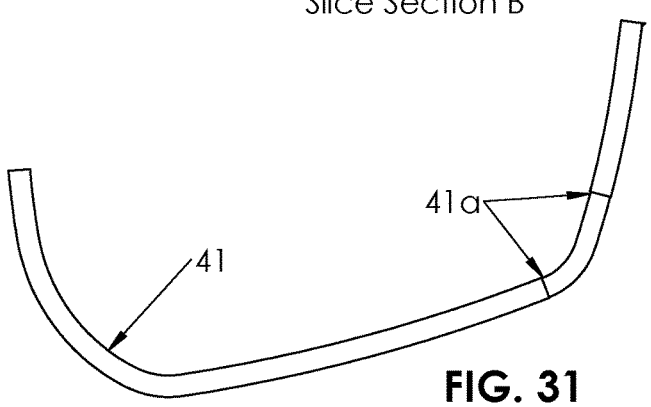
FIG. 31 is a side view of a tube with local reduction in wall thickness.

In FIG. 31 and FIG. 32, tube 41 is disclosed to present the option of having the wall thickness vary along its length. In the section indicated by 41a, the outer diameter of tube 41 has been uniformly reduced, while the inner diameter has remained constant. By changing the wall thickness, the stiffness of the tube is altered to allow it to be more compliant in some areas than others, recognizing that some loss in clamping force may result due to the loss in strength of the tube. Options exist to either increase or reduce the wall thickness only on the inside curvature or the outside curvature of tube 41, thus allowing it to flex more easily in one direction more than the other, and are all part of the preferred embodiment of this invention.

Figure 33:
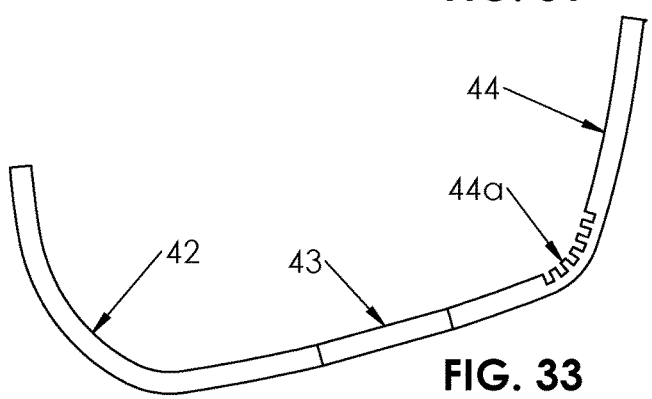
FIG. 33 is a side view of a notched tube.

In FIG. 33, a tube is disclosed to present two additional options; having one or more inserted sections in the tube, and having notches cut into one or more sections of the tube. Both options provide means to allow the tube to be modified more easily when "fitting" the pelvic retainer to a specific user's body. To illustrate the former option, the tube shown comprises tube front section 42, tube mid-section 43 and tube back section 44. The ends the three tube sections fit tightly and connect together with their adjacent section(s), ensuring that cable 7 (not shown) is able to remain tight to the inside curvature and that negligible deflection or rotation occurs at these connecting points. Tube mid-section is shown relatively straight to illustrate this specific variation, both for this sectional tube as well as for the single-piece tube. To illustrate the latter option, notches 44a have been cut into tube back section 44 to allow it to bend more easily. The notches 44a will locally weaken the inside curvature of tube back section 44, but with cable 7 (not shown) under tension, its outward deflection is resisted through the lateral and longitudinal strength of the remaining profile.

Figure 34:
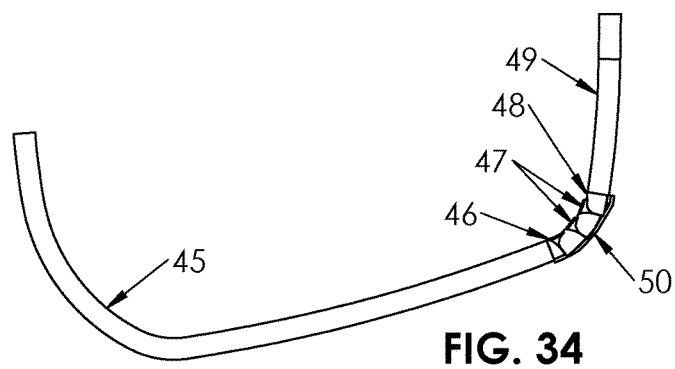
FIG. 34 is a side view of an articulated tube, in the open position.
Figure 35:
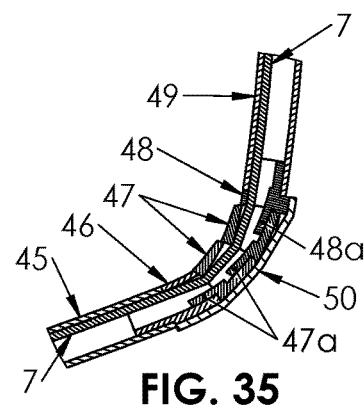
FIG. 35 is a detail mid-section view of the articulated tube in FIG. 34.

In FIG. 34, the option of having a section of the tube articulated is disclosed, with the section that passes around the bottom of the coccyx shown articulated to facilitate ready compliance to that area of the user's body. The novel means of articulation disclosed specifically considers the needs of this application and is not an adaptation of the articulated fingers with hinging phalanges shown in the prior art. Coming from the front support, front tube 45 ends near the back of the perineum. Front tube fitting 46 is fitted into the end of front tube 45 and curves inward as it exits. Links 47 (two are shown, although more are possible) are also inwardly curved and mate to each other as well as to front tube fitting 46. Back tube fitting 48 is fitted into the bottom end of back tube 49, is similarly curved inward and mates to the last link 47. Projecting side walls on links 47 and back tube fitting 48 extend forward over the flattened side portion of bottom tube fitting 46 and of the adjacent links 47 to maintain lateral alignment. The top end of back tube 49 provides the attachment point for the various back supports that have already been disclosed. It is evident that the articulated section could extend fully up to the back support, with back tube fitting 48 directly providing the support for the back support, or that no links 47 are included, and these variations are part of the preferred embodiment of this invention. Finally, resilient member 50 is fitted around the outside curvatures of the fittings 46 and 48 and links 47 and can be either loosely or rigidly attached to some or all of these components. In FIG. 35, cable 7 has been included and it is evident that fittings 46 and 48 and links 47 are hollowed out by curved slots, with cable 7 passing over the high points of each curvature. The outer end of bottom tube fitting 46 has a convex radius which slides on a mating concave radius on the first link 47. Similar convex and concave radii exist on the second link 47, with a concave radius on the back tube fitting 48, and are mated accordingly. Of particular importance is that at least one of the radii at either end is inwardly-biased, meaning that the center line of the radius is angled inward more than the tangential axis of the curvature at the end of the fitting or link. For reference, the upper ends of bottom tube fitting 46 and links 47 are shown inwardly-biased, whereas the bottom ends of links 47 and back tube fitting 48 are not biased. Projection 47a extends from the slot in the first link 47 and fits into the slot in front tube fitting 46, to provide an outward stop for link 47 and ensures that they remain aligned should their respective convex and concave radii become slightly separated when tension is released on cable 7. Projection 47a on the second link 47 and projection 48a on back tube fitting 48 provides a similar function. Resilient member 50 provides the functions of keeping links 47 and back tube fitting 49 together with front tube fitting 46, aids these components to slide outward on their respective radii when tension is released on cable 7 and holds them in the outward position. Resilient member 50 can be optionally made of an elastomeric material or a spring material, and be either under tension or loosely held in order to achieve these functions. External stops could be provided instead of the internal stops shown. Additional interconnecting means to ensure that the fittings and links cannot be separated, such as ribs fitted in mating grooves, or pins traveling in mating slots, can be included and are all part of the preferred embodiment of this invention.

Figure 36:
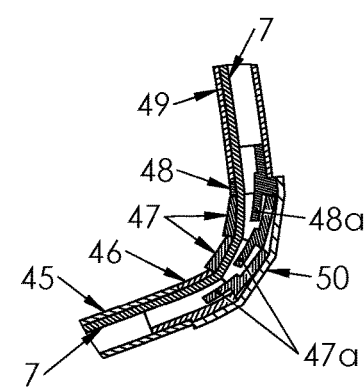
FIG. 36 is a detail mid-section view of the articulated tube in FIG. 34, in a partially closed position.

In FIG. 36, tension has been applied to cable 7, resulting in links 47 and back tube fitting 48 being forced to slide inward on the inwardly-biased radii, reducing the overall curvature of this articulated tube section. With tension maintained on cable 7 while the back support is contacting the body, the inwardly-biased radii on the fittings and links induce lateral forces that resist them from sliding open in order to expand the overall curvature, effectively locking the fittings and links together. This is of critical importance to ensure that the clamping force is maintained and would not occur if the radii were unbiased. When tension is released on cable 7, links 47 and back tube fitting 48 can slide outward, aided by resilient member 50.

All of the options disclosed in FIGS. 29 through 36 can be incorporated into all of the tubes disclosed in this invention and all combinations are part of the preferred embodiment of this invention.

Figure 37:
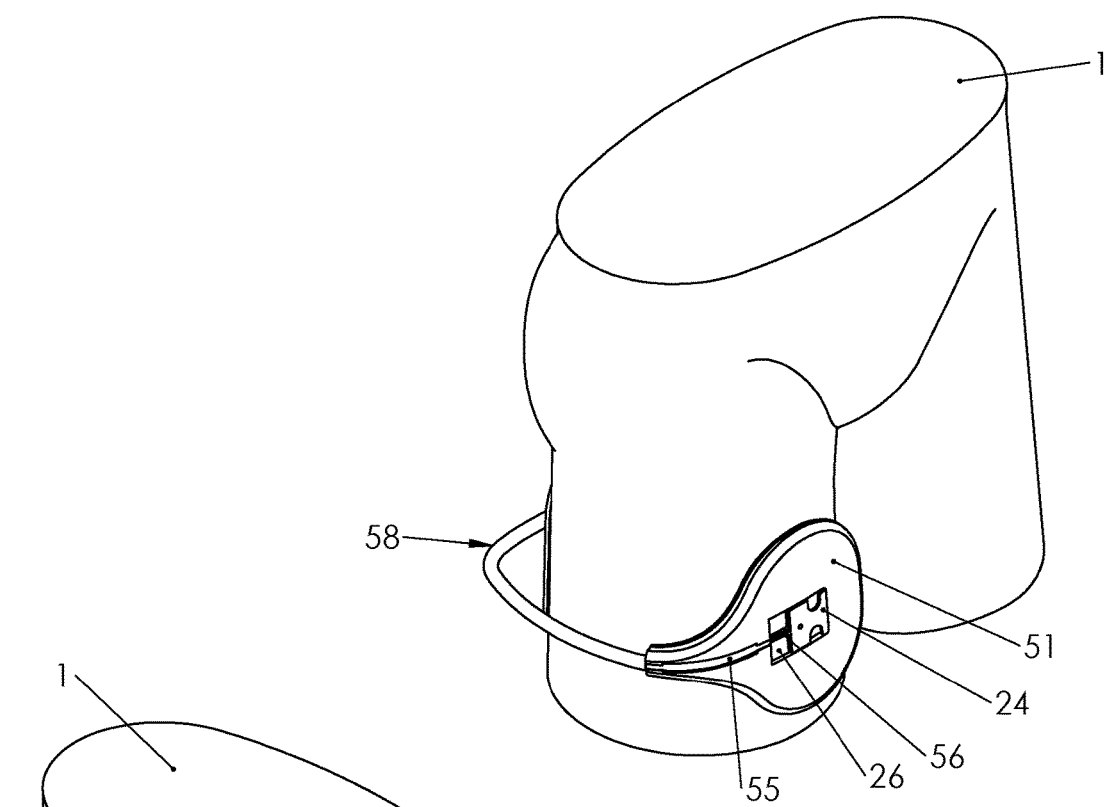
FIG. 37 is a front isometric view of a torso and of a configuration of the leg clamp with a hook-and-loop latch on the front support and an external self-aligning back support, in the closed position.
Figure 38:
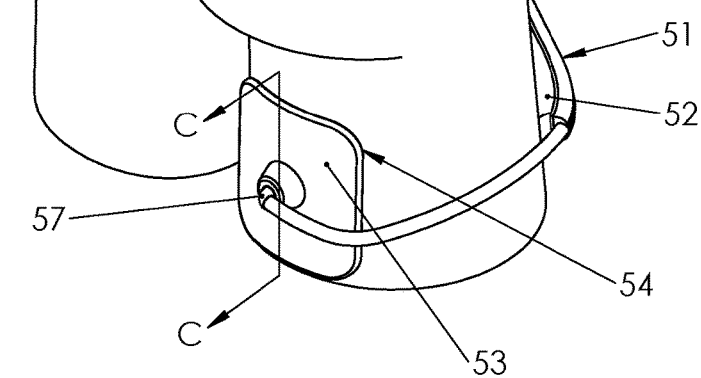
FIG. 38 is a rear isometric view of the same configuration of leg clamp in FIG. 36.

The pelvic retainer shown in the previous figures can be used for specific medical conditions requiring compression in the pelvic region. Another human body clamp is presented in FIG. 37 and FIG. 38 for more general use, in this case as a leg clamp. The emphasis is less on appearance, as it is on utility to provide localized compression on the body. Leg front support 51 forms the front face of the leg clamp, with leg front grip surface 52 contacting one area of the leg (or medical gauze on the leg). Leg self-aligning back support 53 provides the other face of the clamp, with leg back grip surface 54 making contact with the leg (or medical gauze on the leg) generally on the opposite side. Leg front support 51 is shown fitted with a hook-and-loop latch 24 on it, although other cable tensioning means that have already been disclosed can be used. The back end of leg tube 55 is fitted with leg self-aligning tube fitting 57 which contacts leg self-aligning back support 53. The front end of leg tube 55 is held and retained by leg front support 51, and exposed areas of leg tube 55 are covered with hygienic tube cover 58. Leg cable 56 is secured to hook-and-loop latch 24 and retained by its cable lug in leg self-aligning back support 53. Clamping force is generated by applying tension to leg cable 56, which decreases the radii of leg tube 55, forcing leg front support 51 toward leg self-aligning back support 53, as explained previously.

Figure 39:
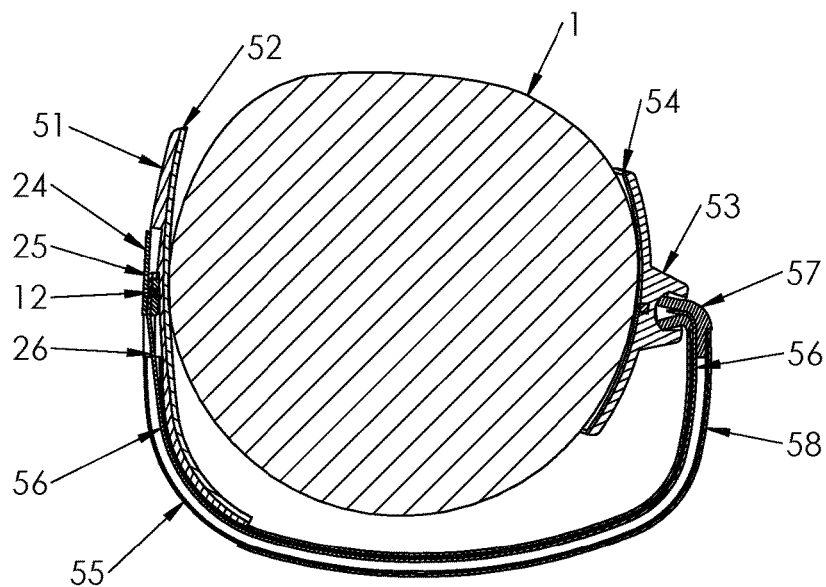
FIG. 39 is a mid-section view of the same configuration of leg clamp in FIG. 36.

The mid-section view in FIG. 39 provides further details on the leg clamp in the closed position. On the left side are leg front support 51 with its leg front grip surface 52 and hook-and-loop 24 in the open position, with its associated components; set-screw 12, latch hook-and-loop 25 and hook-and-loop 26, which function in the ways previously described. On the right side is leg self-aligning back support 53 with its leg back grip surface 54, and details of an outward-facing tapered hole with spherical concave bottom. Leg self-aligning tube fitting 57 forms a right-angle, with one end fitted into leg tube 55 and the other end providing a spherical convex face which mates to the spherical concave surface on leg self-aligning back support 53. Leg self-aligning tube fitting 57 has an inward-facing tapered hole through the center which joins an inward-facing slot in the section that inserts into the end of leg tube 55. Leg cable 56, with its lug seated, passes through a hole in the concave spherical radius in leg self-aligning back support 53 and continues through the tapered hole in self-aligning tube fitting 57 where it is forced by the inward-facing slot against the inside radius of tube 55. The clearances provided between the tapered hole in leg self-aligning tube fitting 57 and leg cable 56, and between the outside of leg self-aligning tube fitting 57 and the tapered hole in leg self-aligning back support 53, allows leg self-aligning back support 53 to adequately pivot unobstructed on its spherical radius. Because the front and back surfaces of the leg are not parallel, leg self-aligning back support 53 is skewed in this mid-section view.

Figure 41:
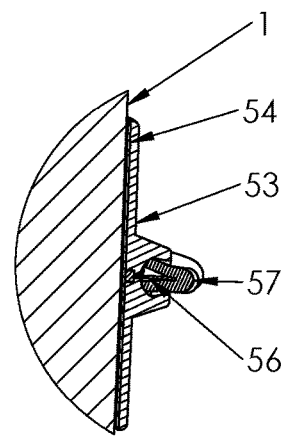
FIG. 41 is a detail section view C of the same configuration of leg clamp in FIG. 36.
Figure 40:
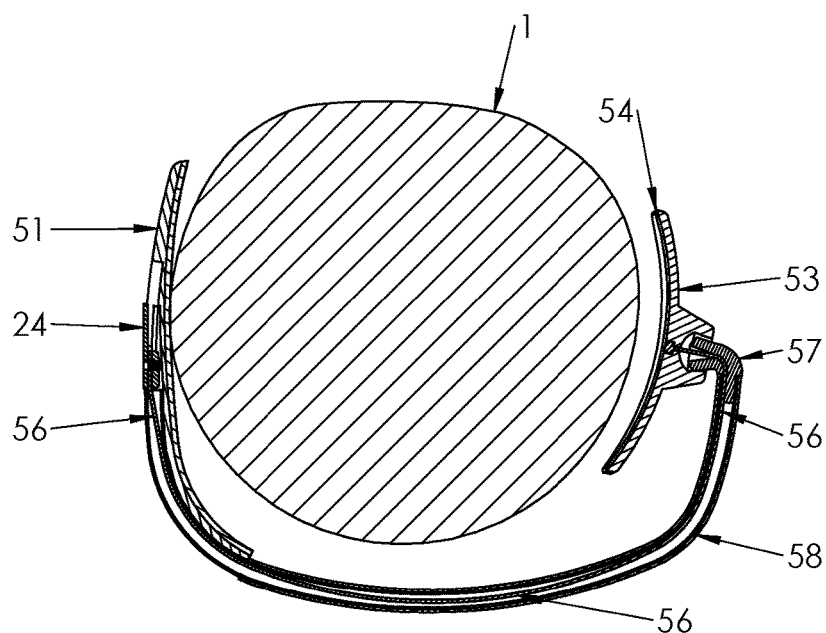
FIG. 40 is a mid-section view of the same configuration of leg clamp in FIG. 36, in the open position.

In FIG. 40, the same components are now shown in the open position. Hook-and-loop latch 24 is in its lowest position, next to leg tube 55 and tension is released on leg cable 56, shown drooping in leg tube 55. Leg tube 55 has sprung open and can be further flexed open to provide additional clearance for leg self-aligning back support 53 to release from the leg. Furthermore, the spherical radius on leg self-aligning back support can release from its mating spherical radius on leg self-aligning tube fitting 57 to provide additional clearance, as shown, yet still remain attached by leg cable 54 in order to immediately re-align when the clamp is closed again. In this view, leg self-aligning back support 53 has been deliberately aligned with leg front support 51 in order to provide a clearer mid-section view through leg self-aligning tube fitting 57. FIG. 41 is a lateral section view which shows the clearances provided between leg cable 56, leg self-aligning tube fitting 57 and leg self-aligning back support 53 that allow it to pivot in any plane. A conventional "ball and socket" design could also be incorporated into leg self-aligning back support 53 and leg self-aligning tube fitting 57, in which the mating spherical surfaces always remain in contact, but the leg clamp could not be opened to the same extent.

The following claims are made about the Invention described in this Application:

1. A retainer or clamp which is configured to contact the body, that provides a controlled clamping force to maintain grip to the skin or controlled pressure on a specific location, comprising:
   a substantially rigid yet resilient front support;
   a substantially rigid yet resilient back support;
   a substantially curved rigid yet resilient tube, which directly or indirectly joins said front support and said back support;
   a cable tensioner on either said front support or said back support;
   a cable which passes through said tube which is secured at one end to said cable tensioner on either said front support or said back support and at the other end to said other support, and when tensioned, remains substantially tight to the inside curvature of said tube.

2. The claim as in claim 1, further in which said cable tensioner has a toggle mechanism.

3. The claim as in claim 1, further in which said cable tensioner is secured by a hook and loop fastener.

4. The claim as in claim 1, further in which said cable tensioner has a linear or rotary ratchet mechanism.

5. The claim as in claim 1, further in which either said support includes a hinge which is configured to allow some or all of said support to pivot toward and away from the body.

6. The claim as in claim 5, further in which said hinge has a substantially vertical slot to allow small lateral rotations of said support.

7. The claim as in claim 1, further in which said back support is able to slide and angularly rotate on said tube, either directly on said tube or indirectly on a fitting on said tube.

8. The claim as in claim 1, further in which said back support and said tube, or a fitting on said tube, include an internal self-aligning feature comprising mating spherical radii.

9. The claim as in claim 8, further in which tension on said cable maintains contact between said mating spherical radii, and said mating spherical radii can be separated when tension is released on said cable.

10. The claim as in claim 1, further in which said back support and said tube, or a fitting on said tube, include an external self-aligning feature comprising mating spherical radii.

11. The claim as in claim 10, further in which tension on said cable maintains contact between said mating spherical radii, and said mating spherical radii can be separated when tension is released on said cable.

12. The claim as in claim 1, further in which said front support and said back support have a grip-enhancing surface which is configured to contact the body.

13. The claim as in claim 12, further in which said grip-enhancing surface is attached in limited locations to said front and back supports, resulting in said grip-enhancing surface being partially suspended off said front and back supports.

14. The claim as in claim 1, further in which the cross-sectional profile of said tube varies along its length.

15. The claim as in claim 1, further in which the wall thickness of said tube varies along its length.

16. The claim as in claim 1, further in which said tube is notched part way through its profile at regions along its length.

17. The claim as in claim 1, further in which said tube comprises two or more sections which fit tightly and connect with each other.

18. The claim as in claim 1, further in which said tube has an articulated section, said articulated section comprising:
a hollow front fitting;
a hollow back fitting;
optional hollow single or multiple links positioned between said fittings;
a resilient member;
further said fittings and links have either concave or convex radii on their ends, that mate with and slide on the opposing radii on said adjacent fittings or links, and at least one said radius on a least one said fitting or link has said radius inwardly-biased such that when tension is applied on said cable passing through said articulated section, said fittings and links are forced to slide inward on themselves,
further said articulated section has an outward position at the point when outward stops on said fittings and links are in contact,
further when tension is released on said cable, said resilient member aids in causing said fittings and links to slide outward on themselves to said outward stops, such that said articulated section is returned to its outward position,
further said fittings and links are laterally aligned.

* * * * *